US007208123B2

(12) United States Patent
Knollenberg et al.

(10) Patent No.: US 7,208,123 B2
(45) Date of Patent: Apr. 24, 2007

(54) MOLECULAR CONTAMINATION MONITORING SYSTEM AND METHOD

(75) Inventors: Brian A. Knollenberg, Superior, CO (US); Daniel Rodier, Louisville, CO (US); Scott Waisanen, Louisville, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 669 days.

(21) Appl. No.: 10/178,818

(22) Filed: Jun. 24, 2002

(65) Prior Publication Data

US 2003/0235926 A1 Dec. 25, 2003

(51) Int. Cl.

| | |
|---|---|
| ***B32B 5/02*** | (2006.01) |
| ***B32B 27/04*** | (2006.01) |
| ***B32B 27/12*** | (2006.01) |
| ***G01N 7/00*** | (2006.01) |
| ***G01N 21/00*** | (2006.01) |

(52) U.S. Cl. ........................... 422/83; 422/50; 422/56; 422/57; 422/58; 422/68.1; 422/81; 422/82.01; 422/82.09; 422/82.11; 422/82.12; 422/88; 422/100; 422/101; 422/102; 422/103; 422/104; 436/43; 436/52; 436/53; 436/149; 436/177; 436/178; 436/179; 436/180; 436/181; 73/1.02; 73/23.2; 73/31.01; 73/31.02; 73/31.03

(58) Field of Classification Search ................. 422/50, 422/56, 57, 58, 68.1, 81, 82.01, 82.02, 82.09, 422/82.11, 82.12, 83, 88, 100, 101, 102, 103, 422/104; 436/43, 52, 53, 149, 177, 178, 436/179, 180, 181; 73/23.2, 31.01, 31.02, 73/31.03, 1.02

See application file for complete search history.

(56) References Cited

U.S. PATENT DOCUMENTS

| | | | | |
|---|---|---|---|---|
| 4,312,180 | A * | 1/1982 | Reif et al. | 60/39.091 |
| 4,743,954 | A * | 5/1988 | Brown | 257/253 |
| 4,808,813 | A * | 2/1989 | Champetier | 356/338 |
| 5,235,236 | A * | 8/1993 | Nakahata et al. | 310/313 R |
| 5,822,883 | A * | 10/1998 | Horwitz | 34/494 |
| 5,918,258 | A * | 6/1999 | Bowers | 73/24.06 |
| 6,321,588 | B1 * | 11/2001 | Bowers et al. | 73/24.01 |
| 6,615,679 | B1 * | 9/2003 | Knollenberg et al. | 73/863.33 |
| 2002/0192117 | A1 * | 12/2002 | Lewis et al. | 422/82.05 |

* cited by examiner

*Primary Examiner*—Brian Sines
(74) *Attorney, Agent, or Firm*—Patton Boggs LLP

(57) ABSTRACT

A flow-through monitor for detecting molecular contamination (MC) within a fluid flow. The monitor has a diffusion chamber having an inlet port and an outlet port, and a structure for supporting a fluid flow from the inlet port to the outlet port. The structure includes a flow gap causing a diffusion of molecular contaminants into the diffusion chamber, while substantially preventing, for a rate of the fluid flow above a predetermined magnitude, particulate contaminants within the fluid from entering the diffusion chamber. A SAW device detects molecular contamination interior to the diffusion chamber. Fluid input to the flow-through monitor may be diluted by a pure fluid for extended monitor life. A system for aggregate sampling connects an ensemble manifold upstream of the flow-through monitor. A system for triggered sampling connects a sample preconcentrator downstream of the flow-through monitor. A chemically selective membrane may be located between the flow gap and the SAW. A test surface adapted to collect MC and located to sample the same fluid as the SAW may also be combined with the monitor. A chemical filter and/or heater may be located upstream of the flow-through monitor and valved to the monitor alternately to the unfiltered and unheated sample.

73 Claims, 11 Drawing Sheets

MOLECULAR CONTAMINATION MONITORING SYSTEM AND METHOD

BACKGROUND OF THE INVENTION

1. Field of the Invention

The present invention relates to monitoring contamination within fluids, and particularly to monitoring molecular and particulate contamination within a flowing fluid.

2. Statement of the Problem

Surface molecular contamination ("SMC") is a phenomenon known in a wide variety of manufacturing fields. SMC is a chemical contamination of a product or component or other surface by gas-phase molecules of any of a variety of contaminants within a fluid contacting the surface. The fluid having the molecular contamination may be a gas or liquid, and is typically the ambient fluid during one or more processing or manufacturing steps. Those skilled in the art distinguish molecular contamination ("MC") from particulate contamination, and we shall make this distinction herein. The difference may be expressed phenomenologically in that particulate contamination does not bond with a surface. While particulate contamination may attach itself to a surface due to static electric charge, when the charge is neutralized, it is easily removed such as by a pressurized stream of gas or by washing with deionized water. On the other hand, molecular contamination is not so easily removed because it can chemically bond with a surface. The difference may also be expressed quantitatively in that particulate contamination is generally on the order of 10 nanometers or greater in size, while molecular contamination is generally on the order of a few nanometers or less. This line is not black and white because, generally, in the field, if a few molecules or more are bound together, the contamination is referred to as "particulate contamination", and the contaminants are referred to as "particles", and the absolute size depends on the size of the molecules. Contamination by molecular contaminants is distinguished from contamination by particles in the art, and will be so distinguished herein. Particles are detected and counted using particle counters, which employ significantly different technologies than MC monitoring. MC molecules have a typical diameter of, for example, 1 nanometer, while a typical particle diameter is 100 nanometers. Surface molecular contamination is sometimes referred to as airborne molecular contamination (AMC) when the perspective is that of the molecular contaminants being present in ambient air, for example in cleanroom air. In this disclosure, SMC includes AMC.

Typical fluid MC compounds are within SEMI F21-95 Classes A, B, C and D. Some, though, are of no particular class. Detrimental effects of SMC occurring due to MC include, for example, changes in the chemical, electrical, and optical qualities of the surface. These manifest in the end product as a decrease in its performance and reliability, and an increase in its cost due to factors including, but not limited to, the lower percentage that pass manufacturing inspections. For example, in the processing and fabrication of a semiconductor, SMC has several detrimental effects. These effects include T-topping of the resist, defective epitaxial growth, unintentional doping, uneven oxide growth, changes in surface properties, corrosion and decreased metal pad adhesion. Many of these are becoming particularly detrimental as line widths less than 0.18 microns are being used. In the optic industry, SMC is a well-known cause of hazing of optical surfaces. SMC also causes friction problems in certain mechanical devices, as SMC contaminated surfaces may have a significantly higher coefficient of friction than uncontaminated surfaces. SMC also affects the manufacture of hard disk drives and flat panel displays which, for reasons known in the art, are typically carried out in a plurality of "mini" clean rooms.

Sources for MC include inadequate filtration of recirculated air, cross-process chemical contamination, outgassing of cleanroom materials, such as filters, gel sealants and construction materials, as well as contaminants carried in and exhuded by human beings. When the fluid is outdoor "make-up" air, the sources of MC include automobile exhaust, evapotranspiration from plants, and various industrial emissions, and the many chemical compounds and vapors resulting from chemical breakdown of, and interaction between, the molecules within the primary sources.

Other sources of AMC/SMC include cross-process chemical contamination within a bay or across a facility, and recirculated air with inadequate ventilation. Still other sources include outgassing by cleanroom materials, such as filters, gel sealants, and construction materials, especially new fabrics, and various contaminants emanating from industrial equipment, such as pumps, motors, robots and containers. Another source is accidents, including chemical spills, and upsets in temperature and humidity controls. Still another source is people, including their bodies, clothes, and their personal care products.

One behavioral characteristic by which SMC is classified is whether it is "reversible" or "irreversible". Reversible SMC increases, or accumulates, when MC exists in a surface's ambient environment, but decreases or evaporates when the surface is no longer exposed to the causative MC. Reversible SMC arises, for example, from MC chemicals with low boiling points, or from contaminant chemicals that do not chemically react with or bond to the surface. Surfaces exposed to such MC types typically re-equilibrate quickly to the MC chemical density within the ambient fluid. Using water as an example MC, dew would be an example of a reversible SMC.

Irreversible SMC, on the other hand, remains on the surface even after the MC is lowered. An example of irreversible SMC is the haze that typically forms on the interior window surface of a new automobile, due to outgassing from the new plastic components in the automobile's interior. The irreversibility is due, generally, to the MC chemical being reactive with the surface and/or the MC chemical having a very high boiling point, (e.g., greater than 150° C.).

FIG. 1 is an example plot of SMC on a measurement surface near a photoresist tool used in the fabrication of an integrated circuit on a semiconductor wafer. The horizontal axis represents time, with the units being days, and the vertical axis represents the SMC density in nanograms per meter squared. The FIG. 1 example shows a first reversible SMC, labeled HV, which occurs as a result of MC arising from high volatility mass deposition events. Due to the high volatility of the MC, the SMC resulting from these events manifests as spikes. FIG. 1 also shows a second reversible SMC, labeled MV, occurring from MC causing medium volatility mass deposition. As shown, the time decay of the MV kind of SMC is slower than that of the high volatility HV SMC. Also shown in FIG. 1 is the steadily increasing level of irreversible SMC, labeled as the trend line LV, arising from MC chemicals having either low volatility or a bonding to the measurement surface.

As seen from FIG. 1, SMC frequently arises from multiple and simultaneous causes. For example, tool maintenance performed near the photoresist tool is an event causing reversible SMC spikes. Another cause is a tool chemical refill operation. The causation is determined in significant part by correlating the time of an SMC event, which is shown by the horizontal axis of the graph, with the time of an activity, such as the above-identified tool maintenance. For this reason, real-time SMC measurements can be very helpful in identifying events that create SMC.

In view of the above-described sources, types and causes of MC and SMC, as well as their effects, many requirements are placed on an MC/SMC monitoring system. These requirements include sensor reliability, chemical selectivity, sensitivity, accuracy in representing MC levels, and the time delay between an MC event and the time that an alert as to the change in the MC/SMC level is generated.

Still another significant requirement is for monitoring of MC within a flowing gas or liquid. A flow having pure fluids is frequently required in manufacturing processes.

There are a number of MC and SMC monitoring systems known in the art, meeting one or more of the above-identified objectives and requirements, but all have significant shortcomings. These include cost, complexity and time requirements for conducting the tests, susceptibility to human error, limitations as to detectable MC species, and poor time resolution. In addition, existing systems cannot typically monitor fluid within a continuous flow. Instead, the existing systems typically monitor a reservoir tank from which the flow originates. Further, many of the existing devices and methods for measuring MC, such as the test wafer method, have a time delay of up to several days. Although this may be tolerable for some applications, there are others where such a time delay is not acceptable.

One known system for measuring MC is the "sorption tube sampling and gas chromatography/mass spectroscopy" method. This system is referenced herein as "GC/MS." For measuring MC in, for example, air, a GC/MS monitoring system pulls a large sample of the air through a sorption tube, which preconcentrates the contaminants. The sorption tube is then thermally desorbed, and the sample flushed into the GC/MS system. The sorption tube, or GC/MS system, may be adequate for detecting some low and mid boiling point organic compounds, typically provides some selectivity as to which MC chemical is to be detected, and has relatively high sensitivity. However, GC/MS is not real-time, meaning that it cannot provide MC readings immediately after a causative event. GC/MS is also time-consuming, involves complex operations, and is susceptible to chemical reactions occurring in the sample apparatus. GC/MS is also typically inadequate at detecting inorganic MC chemicals, and at detecting MC chemicals having a high boiling point.

Other known systems for measuring MC are a "bubbler sampling and impinger ion chromatography" system, referenced herein as "IC", and "atomic absorption spectroscopy," which is referenced herein as "AAS". Typical measurement of, for example, air using AAS or IC begins by pulling a large sample of the air through a liquid bubbler. This obtains, within the liquid, a preconcentration of the air's MC. The liquid is then injected into the IC or AAS system, which detects certain classes of inorganic MC molecules. The AAS and IC methods have good sensitivity and selectivity as to which MC is to be detected. However, like the sorption tube method, the AAS and IC methods are time consuming and do not provide real-time measurements. The AAS and IC methods are also susceptible to chemical reactions occurring in the sample apparatus. Further, they are typically not very good at detecting organic MC chemicals.

A Still another known MC measurement system is the "ion mobility spectrometer," referenced herein as "IMS". In a typical measurement of, for example, air using IMS the air is pulled over a membrane that passes only certain chemicals. The chemicals that pass through the membrane are then ionized by nickel 63. The ions are then separated by their mobility in an electric field.

Chemiluminescence is another known MC measurement system. A typical chemiluminescence system employs ozone within a monitor, which reacts with ammonia/amines to form unstable intermediate molecules. The intermediate molecules decay and, in doing so, generate light which is detected. Chemiluminescence is a real-time MC monitoring technology, with good selectivity and sensitivity. However, it detects only ammonia and amines, and it carries problems in relating the MC data to a particular SMC condition.

Each of the above-identified systems directly measure MC suspended within a sample of the subject fluid. Another class of MC measurement systems and technologies measures surface molecular contamination, or SMC, on a surface exposed to the fluid-born MC.

One known SMC measurement system is the test wafer method, which exposes a test wafer to a fluid for an extended period, typically ranging from three to seven days, removes the wafer and measures it by thermal desorption GC/MS analysis, or by time of flight secondary ion mass spectroscopy, or TOF/SIMS.

The test wafer method solves some of the problems listed above, particularly the scope of MC chemicals that it detects. Basically, the test wafer method can, theoretically anyway, detect anything that stays on the test surface. However, it is not real time, and it has very poor resolution in correlating the time of an MC event to the detected SMC. The test GC/MS analysis method is also inherently deficient in detecting MC species that react with the test surface. It also has shortcomings in detecting MC species having low boiling points, because the SMC for such species is reversible and, therefore, evaporates before the wafer can be tested. Also, if TDGC/MS detection is used to analyze the test wafer, inorganic compounds are not adequately detected.

Another known SMC measurement system is the quartz crystal microbalance system. This system employs a bulk piezoelectric crystal in an oscillating circuit, where the frequency of oscillation changes upon contaminants adsorbing on the crystal surface. In addition, the crystal surface mimics some product surfaces, whereby crystal surface contamination can be monitored overtime using TOF/SIMS or a test wafer to identify a contaminant. However, the sensitivity of the quartz crystal microbalance system, in terms of the frequency change caused by contaminants, is low. Therefore, it is not adequate for typical SMC detection.

Still another known SMC measurement system is the surface acoustic wave ("SAW") sensor system. An example SAW sensor is the commercially available "AiM" monitor from Particle Measuring Systems, Inc. The AiM SAW-based monitor contains two SAW crystals, one having an exposed surface and the other being hermetically sealed. The exposed SAW crystal surface interacts with most MCs of interest in the same way as the surface for which exposure to MCs is of concern. Each SAW is within a resonant circuit, the circuit having a resonant frequency determined, in part, by characteristics of the SAW. SMC on the SAW crystal surface changes its characteristics which, in turn, change the resonant frequency. By comparing the resonant frequency of the circuit having the exposed SAW with the circuit having the sealed SAW, a signal reflecting the amount of SMC on the SAW surface is obtained.

A SAW sensor system such as the AiM monitor satisfies some, but not all, of the objectives required of an MC/SMC monitor system for current and projected industrial needs. For example, the AiM monitor has good sensitivity, and provides real-time SMC data, because the SAW frequency changes as SMC accumulates on its surface. However, the AiM monitor cannot measure MC within a continuous fluid flow.

SOLUTION

The present invention advances the art and overcomes the aforementioned problems by providing real-time monitoring of the molecular contamination within a fluid flow. The invention provides a system that permits molecular contamination in the fluid flow to reach a detector while preventing particulate contaminates from reaching the detector. In the preferred embodiment, a surface of a SAW device is exposed to the molecular contamination and provides a detector signal, a reference SAW that is not exposed to the contamination provides a reference signal, and the detector signal and reference signal are compared to produce a sensor output signal characteristic of the contaminant in the fluid. The sensor signal is preferably corrected for temperature and humidity. Preferably, the molecular contamination monitor is combined with a particle detector to detect both molecular contamination and particle in the fluid in real-time.

The invention provides a molecular contaminant monitoring system comprising: a fluid flow passage; a detection surface; a diffusion structure permitting a molecular contaminant from the fluid in the flow passage to diffuse to the detection surface while preventing particulates in the fluid in the flow passage from reaching the detection surface; and a sensor monitoring the detection surface and providing a sensor output signal characteristic of molecular contaminants on the detection surface. Preferably, the fluid comprises a gas. Preferably, the diffusion structure comprises: a diffusion chamber containing the detection surface; and an opening in the fluid flow passage communicating with the diffusion chamber. Preferably, in one embodiment, the diffusion structure comprises a chemically selective membrane located between the fluid flow passage and the detection surface. Preferably, the invention also includes a hermetically sealed reference chamber; and a reference surface substantially identical to the detection surface, exposed to the interior of the hermetically sealed reference chamber; and the sensor includes: a detector circuit associated with the detection surface and generating a detection signal reflecting a condition of the detection surface; a reference circuit associated with the reference surface and generating a reference signal reflecting a condition of the reference surface; and a comparison circuit receiving the detection signal and the reference signal and generating the sensor output signal reflecting a difference between the detection signal and the reference signal.

In one aspect, the system preferably also includes an environment sensor for detecting at least one of a temperature and a humidity of an externally generated fluid flowing into a diffusion chamber and for generating an environment signal in response; and a compensator processor receiving the environment signal and the sensor output signal, and generating a corrected sensor output signal.

Preferably, in another aspect, the system also includes a particle detector connected to the fluid flow passage.

In a further aspect, the system preferably also includes a heater for heating the fluid.

In still a further aspect, preferably, the system includes a plurality of fluid entry ports connected to the fluid flow passage, and a fluid mixing manifold, the fluid mixing manifold connected between the plurality of entry ports and the fluid flow passage.

In yet another aspect, the system preferably includes a dilution assembly for diluting fluid in the flow passage with a dilution fluid that is substantially free of the contaminant.

In still another aspect, preferably, the system also includes a reference sampler subsystem for alternately sampling to the detection surface the fluid and a reference fluid substantially free of the contaminant.

In yet a further aspect, the system includes a contaminant collection assembly connected to the fluid flow passage. Preferably, in this aspect, the system includes a collection controller subsystem which initiates the collection in response to the sensor output signal either exceeding a predetermined output signal threshold or the rate of change of the sensor output signal exceeding a predetermined rate of change threshold.

In an additional aspect, the system includes a test surface adapted to collect the molecular contamination and located to sample the same fluid as the detection surface.

In the preferred embodiment, the invention provides a molecular contaminant monitoring system comprising: a housing forming a diffusion chamber; a diffusion chamber entry passage extending through the housing; a diffusion chamber exit passage extending through the housing; a detection surface exposed to the interior of the diffusion chamber; and a sensor monitoring the detection surface and providing a sensor output signal characteristic of molecular contaminants on the detection surface; the diffusion chamber entry passage including a diffusion chamber inlet port and a nozzle surrounding the chamber inlet port, and the diffusion chamber exit passage including a diffusion chamber outlet port and a funnel surrounding the chamber outlet port. In this embodiment, the nozzle preferably has a taper T, the funnel also has the same taper T, and the nozzle and funnel are substantially aligned on a common axis.

The invention also provides a method of real-time monitoring of a molecular contaminant in a first fluid, the method comprising: flowing the fluid through a fluid passage; while the fluid is flowing through the passage, diffusing a molecular contaminant within the fluid in the fluid passage into a diffusion chamber at a diffusion rate such that, within a predetermined range of flow rates of the flowing fluid, a level of the molecular contaminant within the diffusion chamber tracks in a known relation with a level of the molecular contaminant within the fluid; detecting the molecular contaminant diffused into the diffusion chamber; and generating a sensor signal characteristic of the level of the molecular contaminant in the fluid. Preferably, the act of detecting comprises: generating a detector acoustic wave on the surface of a detector piezoelectric crystal exposed to the contaminant; and determining a change in the detector acoustic wave due to the contaminant on the surface. Preferably, the act of determining comprises: generating a reference acoustic wave on the surface of a reference piezoelectric crystal substantially identical to the detector piezoelectric crystal and having a surface exposed to a reference fluid, and comparing a parameter of the reference acoustic wave and the detector acoustic wave to provide the sensor signal. Preferably, in one embodiment, the act of generating comprises: detecting at least one of a temperature and a humidity of the fluid and providing a condition signal characteristic of at least one of the temperature and humidity; and adjusting the sensor signal based on the condition signal. Preferably, the fluid is a gas.

In one aspect, the method preferably includes generating a particulate signal characteristic of the particles.

In another aspect, the act of detecting preferably comprises detecting the contaminant on a surface within the diffusion chamber, and the method further comprises reversing a contaminant condition on the surface. Preferably, the act of reversing comprises heating at least a portion of the fluid. Preferably, the act of reversing comprises alternately directing the heated portion of the fluid and an unheated portion of the fluid into the fluid passage. Preferably, this method also includes providing a second fluid substantially free of the molecular contaminant and alternately flowing the first fluid and the second fluid through the fluid passage.

In a further aspect, the method preferably includes the act of diluting the first fluid with a second fluid substantially free of the contaminant. Preferably, the act of diluting comprises: providing a dilution signal indicative of a predetermined ratio of the first fluid and the second fluid; and combining the first fluid and the second fluid in accordance with the dilution signal.

In still a further aspect, the method preferably includes collecting the contaminant in a removable collector. Preferably, the act of collecting includes preconcentrating the contaminant.

In yet another aspect, the method preferably comprises: providing a plurality of sample ports, each receiving a different fluid; and combining the fluids received through the sample ports and outputting the combined resultant fluid to the fluid passage.

In still another aspect, the method preferably comprises: pressurizing the fluid prior to flowing it through the fluid passage; and restricting the flow of the pressurized fluid exiting the fluid passage to provide a predetermined pressure level in the fluid passage.

In yet a further aspect, the method preferably comprises removably securing a test surface in fluid communication with the diffusion chamber.

Numerous other features, objects and advantages of the invention will become apparent from the following description when read in conjunction with the accompanying drawings.

DETAILED DESCRIPTION OF THE PREFERRED EMBODIMENT

1. Overview

The invention is described below with the aid of FIGS. 2–16.

The term “FTA” is used in this description to reference a flow-though MC sensor assembly 10, as opposed to prior art MC sensors, which do not sense MC within a flowing fluid. This assembly comprises the basic molecular contaminant monitoring system 10 according to the invention; other molecular contaminant monitoring systems 100, 120, 130, 150, 160, 170, 180, 190, 600, 700, and 800 according to the invention are shown in FIGS. 6–16. Reference to a particular one of the kinds and variations of FTAs described herein are by unique item number. A reference label of “FTA” means an FTA according to, or as described in reference to, any of FIGS. 2–7 and 9, including all variations and aspects of each, both with and without the various optional features described for each.

The term “fluid” is defined herein as a liquid or gas, or a vapor mixture, including air, elemental gasses such as nitrogen and argon, and mixtures of the same. When an example operation is described, the particular fluid used for the description is not, unless otherwise stated or clear from the context, intended as a limitation on the scope of, or operation of, the invention.

The terms “upstream” and “downstream” are used to specify and define positional relationships with respect to the direction that a fluid flows through the FTA —when the fluid flow occurs. The positional definition remains defined, as such, before the fluid flow through the FTA commences and after the flow ceases.

2. Detailed Description

Figure 2:
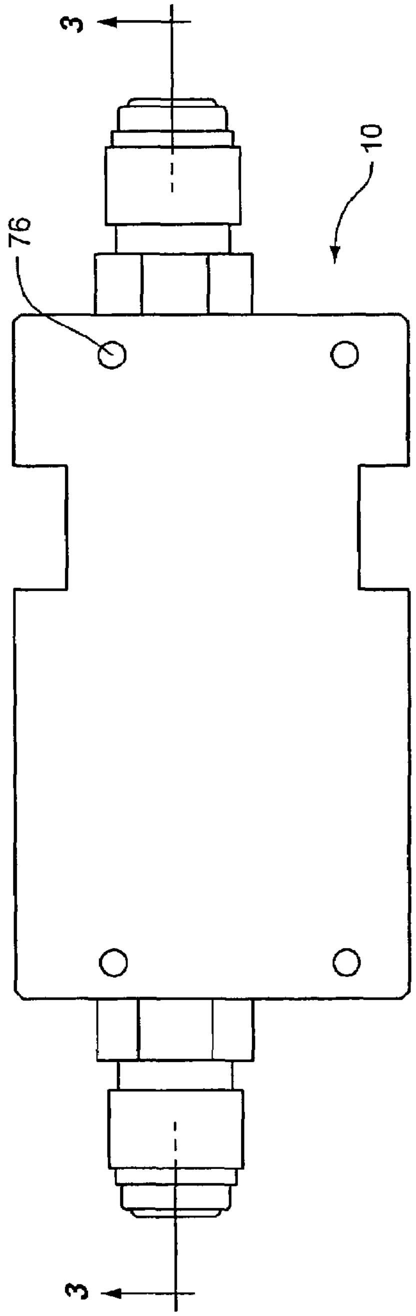
FIG. 2 shows a top view of an example FTA according to the present invention.
Figure 3:
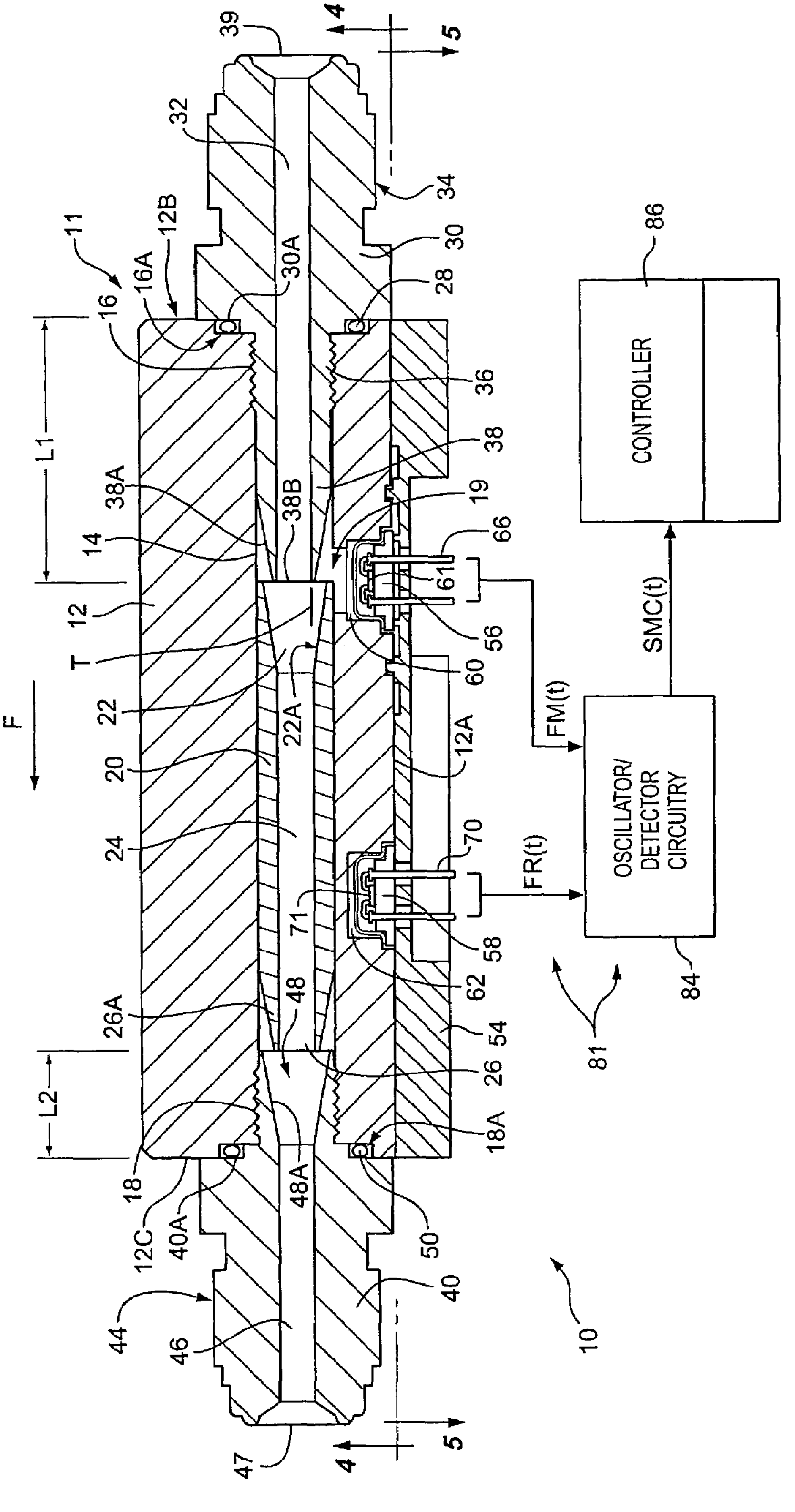
FIG. 3 shows a front cross-sectional view through the FIG. 2 view plane 3—3 of an example FTA according to the present invention.

FIG. 2 shows a top view of an example FTA 10 according to the present invention, and FIG. 3 shows a front cross-sectional view of the depicted example through the FIG. 2 view plane 3—3. Referring to FIG. 3, the example FTA 10 includes a housing 11 having a main body 12 having a main bore 14, the main bore having a threaded influent receptacle 16, and a threaded effluent receptacle 18. A diffusion chamber 19 extends into main bore 14 from a bottom surface 12A of the main body. A center tube 20, which provides a diffusion chamber exit passage 24, is arranged within main bore 14 by, for example, a pressed-in interference fit. Center tube 20 has a diffusion chamber outlet port 22, passage 24, and a center tube outlet port 26. Outlet port 22 preferably has a tapered or funnel-shaped region 22A, the taper having an angle T. An example value of T is twenty degrees. The inside of tapered region 22A preferably has a smooth finish, for purposes of fluid flow and to effect outward flow of particulate contaminants, as described in more detail further below. Similarly, an outer tapered end or nozzle 26A, having a taper angle (not labeled) equal, for example, to T, preferably surrounds outlet port 26 of center tube 20.

Center tube 20 is located such that the inward end of diffusion chamber outlet port 22 is spaced L1 from face 12B of main body 12, which is the face having threaded influent port 16. Center tube 20 extends such that the distal end of nozzle 26A is spaced L2 inward from main body face 12C, which is the face onto which threaded effluent receptacle 18 opens.

Referring to FIG. 3, a recess 16A is formed where threaded influent receptacle 16 opens out to main body face 12B, recess 16A accommodating a first "O" ring 28. An influent member 30 is threaded into threaded influent receptacle 16, the influent member having a receiving port 39, an entry fluid passage 32, an external male connection 34, a threaded shoulder 36, which is the portion threadably engaged with threaded influent receptacle 16, an extension 38 projecting into main bore 14, and terminating at diffusion chamber inlet port 38B. When influent member 30 of the depicted example is threaded into threaded influent receptacle 16 and tightened, first "O" ring 28 is compressed between recess 16A and influent member face 30A, thereby securing influent member 30 and providing a leak-resistance seal.

Influent member 30, which provides a diffusion chamber entry passage 32, has a diffusion chamber inlet port 38B surrounded by an outer tapered nozzle 38A. The form of tapered nozzle 38A may be identical to that of tapered nozzle 26A of center tube 20. As shown in FIG. 3, tapered nozzle 38A and outlet port 38B preferably extend L1 inward of the 12B face, to be substantially coincident in position with the rightmost, or upstream end of diffusion chamber outlet port 22 of center tube 20.

The invention provides a diffusion structure permitting a molecular contaminant from said fluid in said flow passage to diffuse to said detection surface while preventing particulates in said fluid in said flow passage from reaching said detection surface. This structure is preferably provided by nozzle 38A and funnel 22A. The coincident position of tapered nozzle 38A and tapered funnel portion 22A of center tube inlet port 22, together with the angle T of the taper and smooth finish of surface 22A, provide for diffusion of MC into chamber passage 19, while preventing particulate contamination from entering chamber passage 19 and, instead, guiding it through passage 24 of center tube 20 and out of FTA 10. Because particles are by definition hundreds of times larger then molecular contaminants, they have hundreds of times more inertia, and the majority of particles will be funneled into outlet passage 24 and pass out of the FTA. Preferably, within a predetermined range of flow rates of the fluid, substantially all of said particles passing through said entry passage 32 are channeled into exit passage 24. Preferably, this range of flow rates is between 0.0001 cubic feet per minute (cfm) and 100 cfm. That is, there is no substantial statistical probability that a particle contaminant will enter the diffusion chamber. Preferably, the probability is less than 0.1% and, most preferably, less than 0.001% that a particle of size 10 nm or greater will enter the diffusion chamber. The constraints on the particles entering the diffusion chamber are better defined in terms of nanograms per square per day of particulate matter that can deposit on detector surface 61. Preferably, 0.05 nanograms or less per day of particulate matter will deposit on the surface and, more preferably, 0.01 nanograms or less. Any particulate contamination of the order of magnitude of the molecular contamination would tend to mask the molecular contamination; thus, the range of particulate contamination that would be acceptable will vary depending on the location of the detector. Generally, in a normal environment, the deposition of molecular contamination on surface 61 is of the order of 0.15 nanograms per square per day, although this can, of course, be much greater in dirty environments and much less in a very clean environment, such as a high level cleanroom. At the same time, the diffusion structure permits sufficient diffusion of molecular contaminants into diffusion chamber 19 so that SAW sensor system 81 can detect the contamination in surface 61. Further, the above-described structure of tapered nozzle 38A and tapered portion 22A of center tube inlet port 22 permit molecular contaminants to diffuse into diffusion chamber passage 19 without obstructing the flow of fluid through the FTA. Because of the diffusion, the concentration of molecular contaminants within the diffusion chamber passage tracks in substantial equilibrium with the concentration of molecular contaminants within the fluid. As described in greater detail below, sensors perform real-time detection of the molecular contaminants in diffusion chamber 19. Accordingly, this invention provides continuous real-time detection of molecular contaminants within a continuously flowing fluid. This is one of the significant advantages of this invention over the prior art.

Another significant feature and advantage is that the taper angle T would force particulate matter in the fluid flow exiting influent tube 32 at nozzle 38A to make a near ninety degree turn after striking surface 22A for that particulate matter to enter diffusion chamber passage 19. Because of the mass and velocity of the particles and the smoothness of surface 22A, however, the particles' momentum will substantially prevent the particles from undergoing such a turn. The particles will, instead, be guided by surface 22A to enter and continue through passage 24 of center tube 20 and out though effluent tube 46 to exit port 47. Therefore, the particles will pass through FTA 10 instead of contaminating the MC detection means within FTA 10, which is described below. As will also be described in reference to further aspects of this invention, a particulate contaminant counter may be attached downstream of the FTA, thereby exploiting the FTA's feature of passing the particulate contaminants.

It will be understood that the positional relationship between nozzle 38A and port, region 22A, as well as the taper angle T, depend in part on the diameter (not labeled) of influent passage 32 and exit passage 24 of center tube 20, respectively, and on the pressure and/or velocity of the fluid entering influent tube 32 through nozzle 38A. If the spacing between nozzle 38A and port region 22A is too large, the fluid flow will be interfered with or disrupted, and particulate contaminants will not be effectively guided out of FTA 10 by surface 22A. If the spacing is too small, the diffusion rate will be too slow, which will tend to degrade its real-time monitoring performance.

Referring to FIG. 3, the outer contour of external male connection 34 is in accordance with known design practices for connections onto which a flexible tube (not shown) or equivalent would attach. Also, the relation between the diameter (not numbered) of main bore 14 and the outer diameter (not numbered) of influent member 30 extension 38 is preferably selected to provide a snug fit, with no substantial volume between the outer surface of extension 38 and the inner surface of main bore 14 in which fluids could accumulate.

The exemplary FTA 10 of FIGS. 2 and 3 further includes an effluent member 40, having a through hole or passage 46, an exit port 47, and an external male connection 44, the effluent tube 46 having a threaded exterior 48. Threaded exterior 48 is engaged with threaded effluent receptacle 18. A recess 18A is formed where threaded effluent receptacle 18 opens out to main body face 12C, recess 18A accommodating a second “O” ring 50. When tightened, face 40A of effluent member 40 compresses second “O” ring 50 against recess 18A. In the example depicted by FIG. 3, effluent tube 46 has an inlet port 48 having a tapered opening 48A. An example taper (not labeled) of tapered opening 48A would be the same as the taper angle T of inlet port 22A of center tube 20. Effluent tube 46 extends a distance L2 inward of main body face 12C, to be substantially coterminous in the flow direction F with nozzle 26A of center tube 20.

The outer contour (not labeled) of each of the external male connections 34 and 44 is in accordance with standard design practices for tube connections as are known in the art. External male connection 34 and external male connection 44 are depicted, for purposes of describing the invention with basic examples, as having the same diameter. However, this is not intended as any limitation on the structures by which this invention can be carried out. Applications of this invention are contemplated which use external connections 34 and 44 having respective diameters that are not equal to one another.

A preferable material for main body 12 is “316” stainless steel. Aluminum, may also be used for ease of manufacture and reduced weight. Preferably, the body material, if formed of aluminum or the like, is plated with, for example, gold to provide an inert, corrosion resistant surface.

Figure 4:
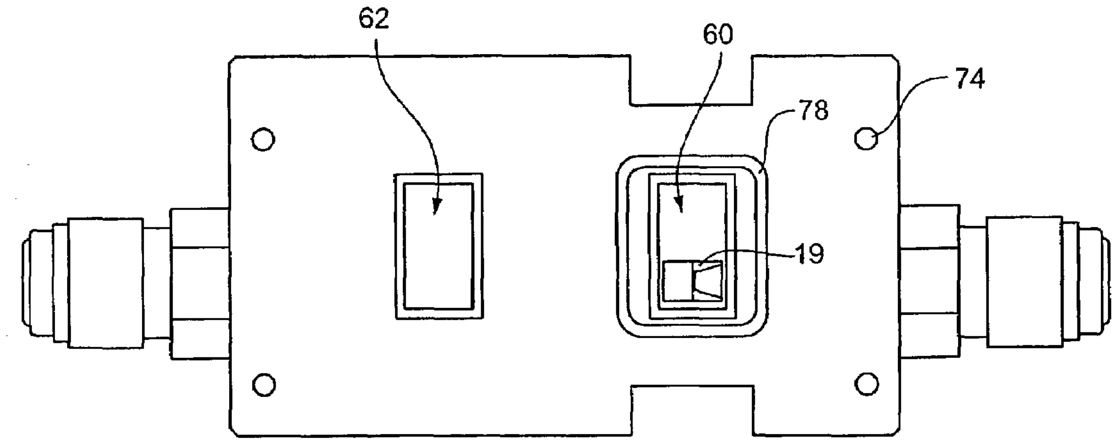
FIG. 4 shows a bottom view of a center body of the FTA according to FIGS. 2 and 3.
Figure 5:
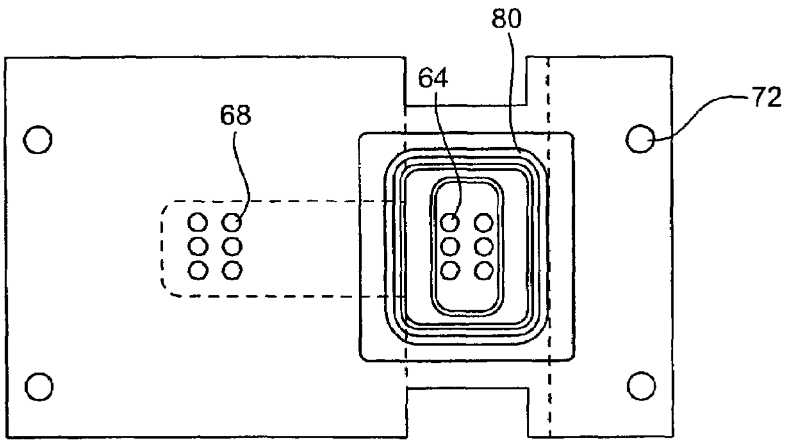
FIG. 5 depicts a top view of the base plate of the example FTA depicted in FIGS. 2 and 3.

Referring to FIG. 3, a base plate 54 attaches to bottom 12A of main body 12. FIG. 4 is a view of bottom 12A of main body 12, to which base plate 54 attaches, seen from the FIG. 3 view line 4—4. FIG. 5 is a top view of base plate 54, seen from the FIG. 3 cut line 5—5. Base plate 54 supports a measurement SAW 56 and a reference SAW 58 (FIG. 3). SAWs 56, 58 are described in greater detail below. A first recess 60 is formed in main body 12 which, as seen in FIG. 4, is aligned with diffusion chamber passage 19. First recess 60 accommodates measurement SAW 56 so that the SAW upper surface 61 is exposed to diffusion chamber passage 19. A second recess forming reference chamber 62 accommodates reference SAW 58. Referring to FIGS. 3 and 5, a plurality of clearance through holes 64 in base plate 54 accommodate a plurality of pins 66 extending from measurement SAW 56. Similarly, a plurality of clearance holes 68 accommodate a plurality of pins 70 extending from reference SAW 58.

In one embodiment, base plate 54 has a plurality of threaded holes 72 corresponding in position to a plurality of clearance holes 74 formed in main body 12. In this embodiment, base plate 54 is secured to bottom 12A of main body 12 by screws which extend through main body 12, with example screw heads labeled as item 76 in FIG. 2. In another embodiment (not shown), base plate 54 and main body 12 are held together by a single rotating knob that has ramps around its outer edge. As the knob is turned, the ramps act to clamp the base plate and main body together. This facilitates faster and easier closing and opening of the FTA.

Referring to FIGS. 4 and 5, a groove 78 is formed in bottom surface 12A of main body 12 around first recess 60, and corresponding ridge 80 is formed in base plate 54 surrounding the area on which pin clearance holes 64 are formed, which is where measurement SAW 56 is supported. Ridge 80 and groove 78 fit together with a Teflon™ gasket squeezed between them, when base plate 54 is attached to main body surface 12A, to prevent leakage into or out of diffusion chamber passage 19.

It will be understood that the structure of the example FTA 10 that is shown in FIGS. 2–5 is only for purposes of example. Various alternative structures within the scope of the appended claims are contemplated by this invention and will be identified upon reading this disclosure. For example, nozzle 26A on the outlet port of center tube 20 could extend substantially into tapered inlet port 48A of effluent member 40. Another variation is that, instead of center tube 20 and effluent member 40 being separate structures, the two could be combined into a unitary member (not shown). Yet another variation is that, instead of influent tube 38 being integral with influent member 30, the influent tube could be a separate item (not shown) extending through an equivalent to male connection 34. Such an equivalent to male connection 34 would, for example, be a two-piece unit (not shown), functioning as a threaded tube clamp (not shown) which, when tightened, would secure the separate influent tube (not shown) from axial motion.

A preferable material for influent member 30 and effluent member 40 is type “316” stainless steel. Alternative materials can be selected by one of ordinary skill using, as general selection criteria, cost, ease of machining, and the chemical and mechanical properties dictated by the function of this invention.

The detection of molecular contaminants within diffusion chamber passage 19 is preferably performed by an electronic sensor circuit 81 having a piezoelectric crystal element, such as SAW 56, with the crystal having a surface 61 exposed to diffusion chamber passage 19. SMC that accumulates on the exposed surface of the piezoelectric crystal such as, for example, SAW 56, as a result of MC in the diffusion chamber changes the electrical characteristics of the piezoelectric crystal, which causes a detectable change in the electronic circuit. This invention, however, is not limited to any specific method for detecting the MC within diffusion chamber passage 19.

An exemplary sensor 81 for detecting MC within diffusion chamber passage 19 includes a SAW system having SAWs 56 and 58, frequency generation/detection circuit 84, and controller 86. SAW device 56 and circuitry 84 comprises a detection circuit associated with detection surface 61. SAW 58 and circuitry 84 comprises a reference circuit associated with reference surface 71. A comparison circuit within circuit 84 generates a sensor output signal SMC(t) reflecting a difference between the detection signal and the reference signal. Thus, this signal is characteristic of the level of the contaminant in the fluid. Frequency generation/detection circuit 84 excites an oscillation within each of SAWs 56, 58, using circuitry and techniques that are known to persons skilled in the arts to which this invention pertains. An example of a frequency generation/detection circuit that may be used for item 84 is described as items 29 and 31 in U.S. Pat. No. 5,476,002, issued to Bowers et al., which is hereby incorporated by reference. A signal representative of the oscillating frequency of measurement SAW 56 at time t is shown as FM(t), and a signal representative of the oscillating frequency of reference SAW 58 at time t is shown as FR(t). As known to persons skilled in the relevant arts, the frequency at which SAWs 56, 58 will oscillate, i.e., FM(t) and FR(t), depends on the physical characteristics of the SAW, and on the crystals' age and temperature. SAWs 56, 58 are preferably of identical specification. Therefore, changes in their respective oscillation frequency due to age and temperature are substantially identical. As is also known to one skilled in the art, the surface acoustic wave frequency of a SAW such as item 56 changes when SMC manifests on its surface. Since reference SAW 58 is hermetically sealed, however, its surface cannot be contaminated by the MC. The surface of measurement SAW 56, on the other hand, is exposed to the interior of diffusion chamber passage 19. Molecular contaminants that have diffused into diffusion chamber passage 19 will therefore cause SMC on the exposed surface of SAW 56. The oscillation frequency FM(t) will change as a result of this SMC. Detection circuitry 84 detects this change by comparing FM(t) and FR(t) and generates an SMC(t) signal representative of their difference and, therefore, representative of SMC on the surface of SAW 56.

Sensor circuit 81 also includes general purpose programmable computer 86 for receiving and storing SMC(t), and other sensor data such as, for example, data from temperature and humidity sensors 102 described below. It will be further understood that blocks 84 and 86 are shown as separate blocks only for purposes of describing their respective functions. Upon reading this disclosure, one of ordinary skill in the art will understand that the functions of blocks 84 and 86 can be combined into a single circuit and/or circuit package. Further, the functions of blocks 84 and 86 may be distributed among various arrangements of hardware circuits.

Computer 86 may, for example, be a standard Intel® Pentium® based general purpose programmable computer having a standard commercially available interface card for receiving and formatting signals such as FM(t), FR(t), SMC(t), and other sensor data from the FTA, and running under, for example, the Windows® XP operating system.

Figure 1:
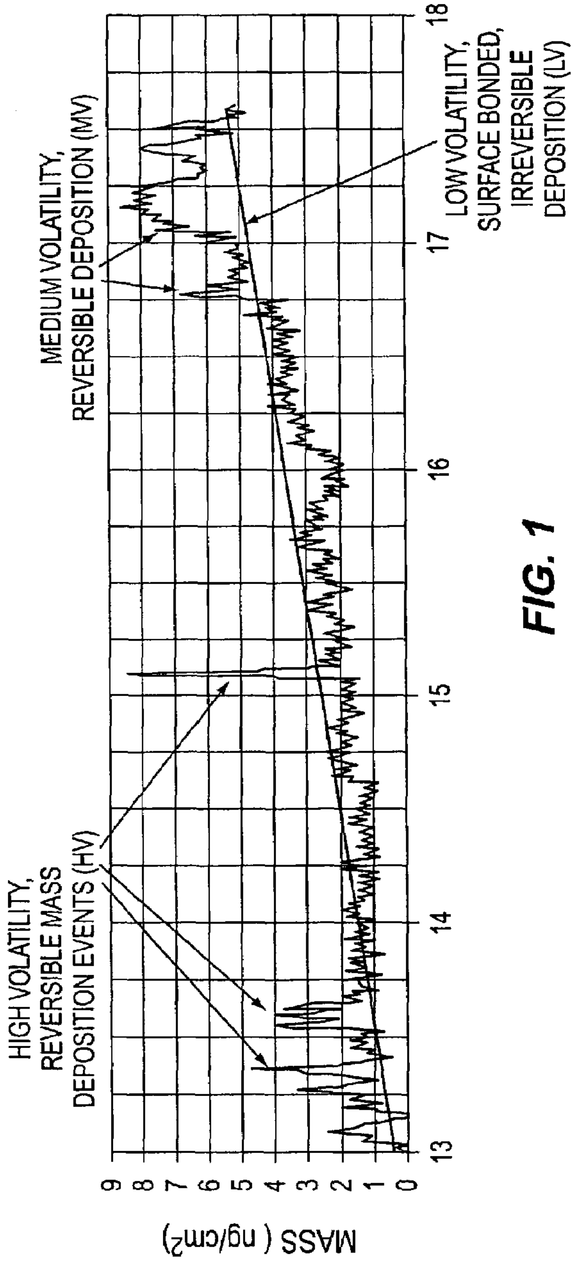
FIG. 1 depicts an example SMC on a measurement surface near a photoresist tool.

Depending on design choice, computer 86 may generate an alarm (not shown) based on SMC(t). Preferably, the alarm is based on a combination of the magnitude of SMC(t), and its rate of change. Referring to FIG. 1, the reason that the alarm should be based, at least in part, on the rate of change of SMC(t) is that certain MCs cause irreversible SMC on the surface of, for example, SAW 56. In such a case, as seen from FIG. 1, the SMC(t) value will steadily increase over time, even in the presence of acceptable levels of MC in the subject fluid. Therefore, preferably, the alarm is not based solely on a fixed threshold value of SMC(t). Instead, the alarm preferably is based on a combination of the magnitude and rate of change of SMC(t), readily implemented by computer 86 using standard software coding methods.

The media of the alarm is also a design choice. Preferably, data indicative of an alarm would be stored in the test record storage media (not shown) of computer 86. It is also contemplated that an audio alarm may be generated, notifying or cueing, for example; manual shut-off of the manufacturing process relating to the fluid flowing through the FTA, and immediate investigation into the alarm's causative event.

Figure 6:
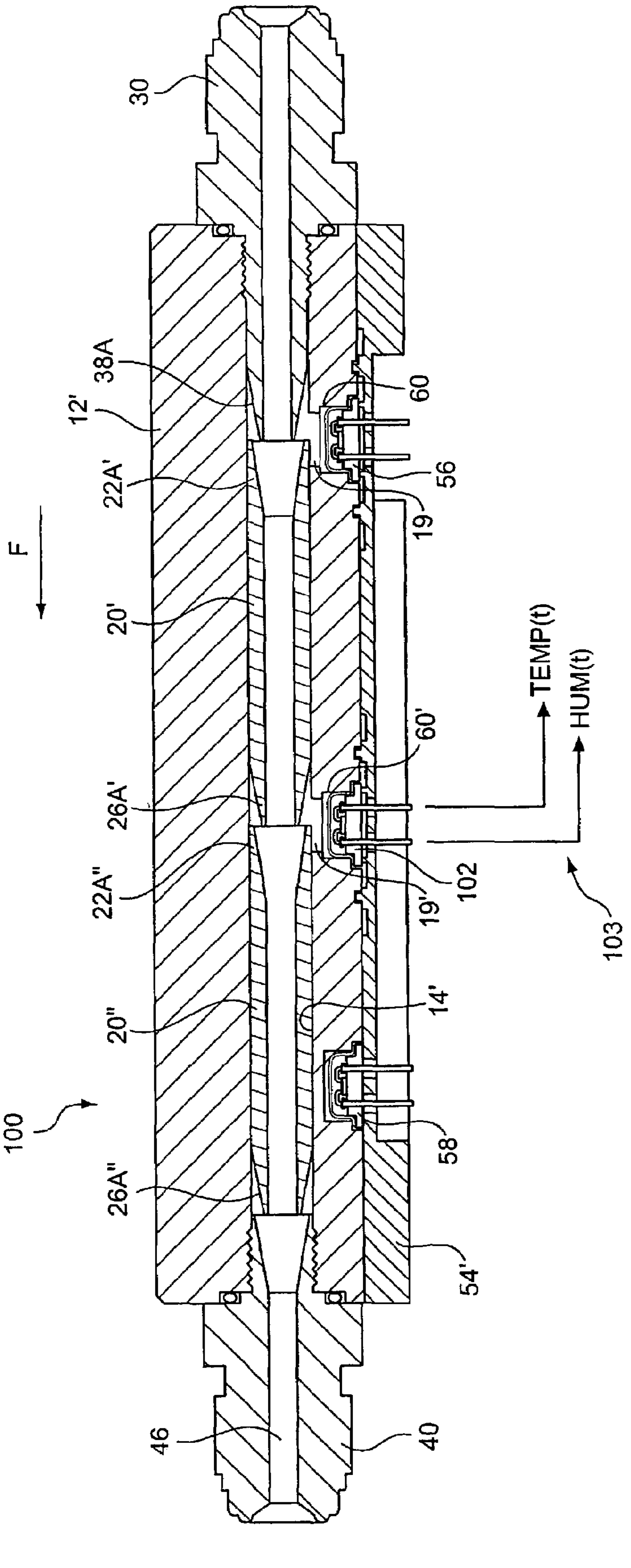
FIG. 6 depicts another aspect of the invention, comprising an FTA similar to that of FIG. 3, except that it includes a temperature/humidity sensor and a second diffusion chamber.

FIG. 6 shows an alternate embodiment of an FTA 100 according to this invention. FTA 100 has similarity with the FTA embodiment depicted by FIGS.2–5 and, accordingly, like structures are labeled with like reference numbers. Referring to FIG. 6, the significant feature of item 100 FTA is an environmental sensor 102 which preferably is a temperature/humidity sensor 102. Sensor 102 detects the temperature and humidity of fluids passing through the FTA, and it outputs environmental signals TEMP(t) and HUM(t) 103, reflecting the temperature and humidity, respectively, at time t. The reason for sensor 102 is that temperature and humidity levels at the exposed surface of SAW 56 affect the manner in which molecules of the MC will partition between the fluid and the surface. More specifically, the temperature and humidity levels of the fluid typically shift the fluid-to-surface equilibrium. As a result, the amount of SMC on the surface resulting from MC within diffusion chamber passage 19 may depend, in part, on the temperature/humidity of the fluid. Therefore, to compensate for the effects of temperature and humidity, the compensator processor 86 may receive one or both of sensor 102 signals TEMP(t) and HUM(t), and uses one or both of these signals in calibrating or adjusting the SMC(t) signal.

The FIG. 6 example structure has a center body labeled 12' which differs from the FIGS. 3 and 4 center body 12 by having a longer main bore, labeled 14', with a second diffusion chamber passage, labeled 19', and a third recess, labeled as item 60'. Base plate 54' differs from the FIG. 5 base plate 54 by having an area (not numbered) for supporting sensor 102, and by having through holes for accommodating sensor pins 104. To provide a path by which sensor 102 is in fluid communication with the flow through the FTA, a first center tube, labeled 20', and a second center tube, labeled, 20" are substituted for the single center tube 20 shown in FIG. 3. For inventory purposes, center tubes 20' and 20" may be identical to one another. The structural relation between the tapered inlet port 22A' of first center tube 20' and the tapered nozzle 38A surrounding the outlet port of influent tube 38 is the same as that described between tapered nozzle 38A and inlet 22A described in reference to FIG. 3. The structural relation between tapered nozzle 26A' and the outlet of first center tube 20' and the tapered inlet port 22A" of second centertube 20" may be the same as that between items 38A and 22A'. The reason for the similarity in these structural relationships is that the relation between tapered nozzle 26A' and tapered inlet port 22A" is to permit fluid communication with sensor 102 without interfering with the fluid flow through the FTA, while preferably preventing particulate contamination from entering and building up within second diffusion passage 19'.

Referring to FIG. 6, although it is contemplated by the invention that the temperature/humidity sensor 102 could be located in a position that is not isolated from the diffusion chamber 19, it is preferable that temperature/humidity sensor 102 be located in a chamber that is substantially isolated from diffusion chamber passage 19 in which the exposed face of SAW 56 is located. A significant reason for this isolation is that contaminant molecules may emanate from sensor 102. If sensor 102 and the exposed face of measurement SAW 56 were located in a common chamber, such molecules could, possibly, be mistaken for contaminants that diffused from the sample fluid. Therefore, temperature/humidity sensor 102 is, in the FIG. 6 example, located in a second chamber 19' formed by the third recess 60' after base plate 54' is installed. Temperature/humidity sensor 102 is shown located downstream of the diffusion chamber 19 and sensor 56. It also could be located upstream of the sensor 56 or any other convenient location.

Figure 7:
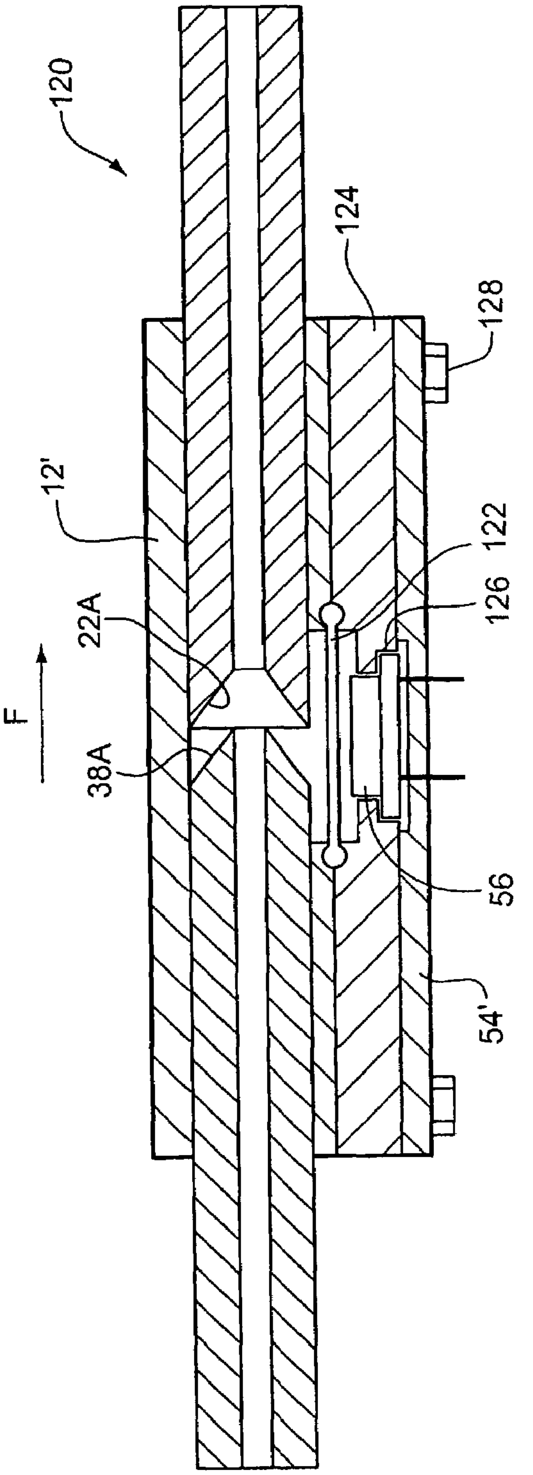
FIG. 7 depicts another aspect of the invention, comprising an FTA according to any one or more of FIGS. 2–5, and 6, further including a chemically selective membrane.

FIG. 7 shows another FTA 120 in accordance with this invention. Comparing FIG. 7 to FIGS. 2–6, FIG. 7 is a simplified view, omitting structures described and shown in FIGS. 2–6 and, for purposes of this description, showing only the details specific to FTA 120. Referring to FIG. 7, the significant feature of the FTA 120 is a chemically selective membrane 122 interposed between diffusion chamber passage 19 and recess 60 in which the detection surface of measurement SAW 56 is exposed. Chemically selective membrane 122 provides a contaminant-specific detection feature for the FTA of this invention, even though SAW 56 does not, itself, typically distinguish as to which type of SMC is on its surface.

Chemically selective membrane 122 is removably secured within the FTA 120 by inserting an intermediate plate 124 between base plate 54 of FIGS. 3 and 5 and center body 12, or between membrane plate 54' and center body 12' of FIG. 6. Intermediate plate 124 has a through hole 126 for each SAW supported on base plate 54 (or 54'), as well as any sensor, such as item 102 of FIG. 6. Intermediate plate 124 may be clamped between base plate 54 and body 12 by screws or a rotating knob as described in reference to FIGS. 4 and 5. Alternatively plate 54' may be a separate plate from base plate 54 and intermediate plate 124 may be attached by four bolts 128 which clamp intermediate plate 124 between membrane plate 54' and main body 12' as shown in FIG. 7, thereby clamping chemically selective membrane 122 over measurement SAW 56. The FIG. 7 example structure for removably securing chemically selective membrane 122 permits ready replacement of the membrane, either by another of the same kind, or by a membrane that passes or blocks different types of molecules.

Chemically selective membrane materials suitable for item 122 are available from a number of commercial sources. A detailed description of their materials, chemical selectivity characteristics and operation is, therefore, not necessary. As a general overview, however, it is understood by persons skilled in the art that most chemically selective membranes pass or do not pass gas molecules based on the solubility of the molecules in the membrane material. For example, non-polar (hydrophobic) materials will pass non-polar molecules such as hydrocarbons. Polar (hydrophilic) materials will pass polar compounds such as polar organics (generally small molecules) and inorganic molecules. Additionally, ion exchange membranes can be used for polar compounds. Specific additives can also be incorporated into the membrane, such as chelating agents, metals that form complexes with, for example, nitrogen compounds.

Figure 8:
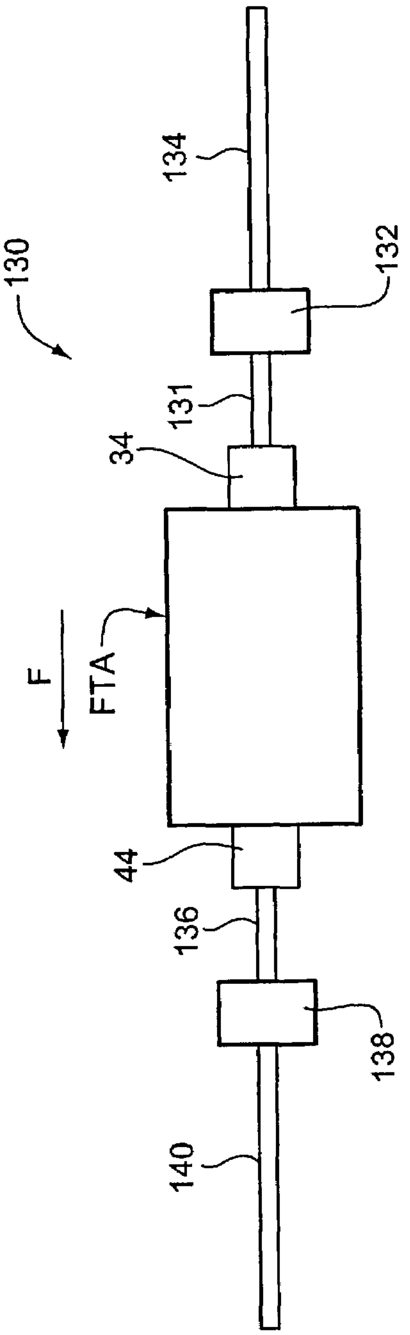
FIG. 8 depicts a further aspect of the invention, having an FTA according to the invention connected into a gas line, for monitoring a pressurized gas flow.

FIG. 8 shows an example application of an FTA in a molecular contaminant monitoring system 130 according to this invention connected in line with an external fluid line, for monitoring MC within an unregulated fluid flow. Referring to FIG. 8, the depicted example includes an FTA according to this invention, with an influent connector 34 connected to a first external influent tube 131, which is connected through a conventional tube connector 132 to an external fluid source line 134. FTA effluent connector 44 is connected to a first external effluent tube 136 which connects, through another conventional tube connector 138, to an external fluid feed line 140. Outputs from measurement SAW 56 and reference SAW 58 (not shown in FIG. 8) and, if used, temperature/humidity sensor 102, are received by a data processor (not shown) such as, for example, the computer 86 of FIG. 2.

Figure 9:
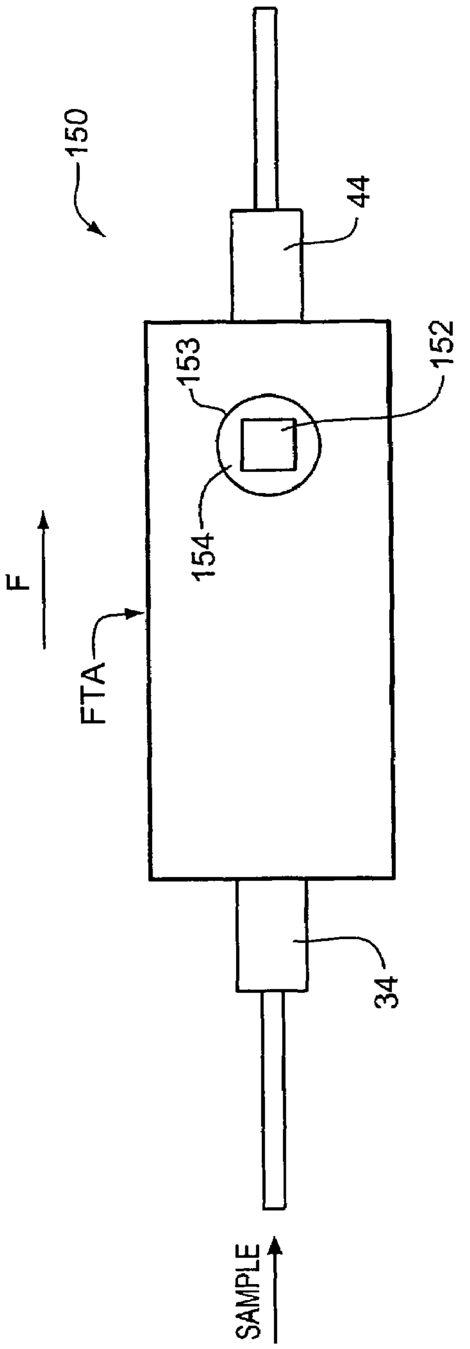
FIG. 9 depicts another aspect of the invention, comprising an FTA according to any one or more of FIGS. 2–5, 6 and 7, further including a witness window and test wafer feature.

FIG. 9 shows another variation of an FTA monitoring system 150 according to this invention. The additional feature of the FIG. 9 FTA is a witness surface, or test surface 152 which is inserted into the FTA through a portal 153 having a removable cover 154. The FIG. 9 FTA exposes test surface 152 within a third chamber (not shown), which is connected by a passage (not shown) to the FIG. 3 diffusion chamber passage 19 (not shown in FIG. 9), or to the second diffusion chamber passage 19' of FIG. 6, or to another diffusion chamber passage (not shown) structured as described for passages 19 and 19', to be in fluid contact with the same fluid that contacts the surface of measurement SAW 56.

It should be understood that if chemically selective membrane 122 of FIG. 7 is included, then, preferably, test surface 152 is exposed to post-membrane fluid, either within the same diffusion chamber passage as measurement SAW 56, or in a separate diffusion chamber (not shown). Preferably, the exposed surface of test surface 152 has chemical and physical properties, at least with respect to interactions with the kinds of MC that are of interest, that are identical to those of the exposed surface of measurement SAW 56. Having such properties, MC that causes SMC on the surface of SAW 56 will cause substantially the same SMC on the exposed surface of test surface 152. This enables the user of the FIG. 9 FTA to determine, in many instances, the kind of MC that caused an increase in the SMC(t) signal and, if an alarm is used, the MC that cause it to be generated.

An example operation of the FIG. 9 FTA will be described. For this example, it will be assumed that an external flow (not shown) is connected to external influent connector 34. It is also assumed that the MC within the fluid has been at an acceptable level, but that an irreversible SMC has been accumulating on the surface of measurement SAW 56. The SMC(t) signal would, therefore, have shown a substantially monotonic increase in level, over a time period of, for example, five days. Then, at a time referenced herein as $t_1$, it is assumed that an event occurs causing a remarkable increase in the MC level of the fluid entering influent tube 38. The increased MC will quickly, by means of the spacing between nozzle 38A and inlet port 22A of center tube 20, diffuse into and cause a similar increase in the MC within diffusion chamber passage 19. This, in turn, will manifest as a high-rate increase in the SMC on the surface of SAW 56, causing the frequency FM(t) to change at a substantially increased rate. Therefore, as described above, an alarm will be generated by the computer 86. In response, the flow through FTA 150 could be shut off, either automatically or manually, depending on design choice, and test surface 152 removed. Test surface 152 may then be analyzed to identify the MC. To further assist in identifying, and characterizing, the physical event, the humidity sensor signal, HUM(t), and the temperature sensor signal, TEMP(t), if recorded as described above, may also be obtained for time $t_1$.

Figure 10:
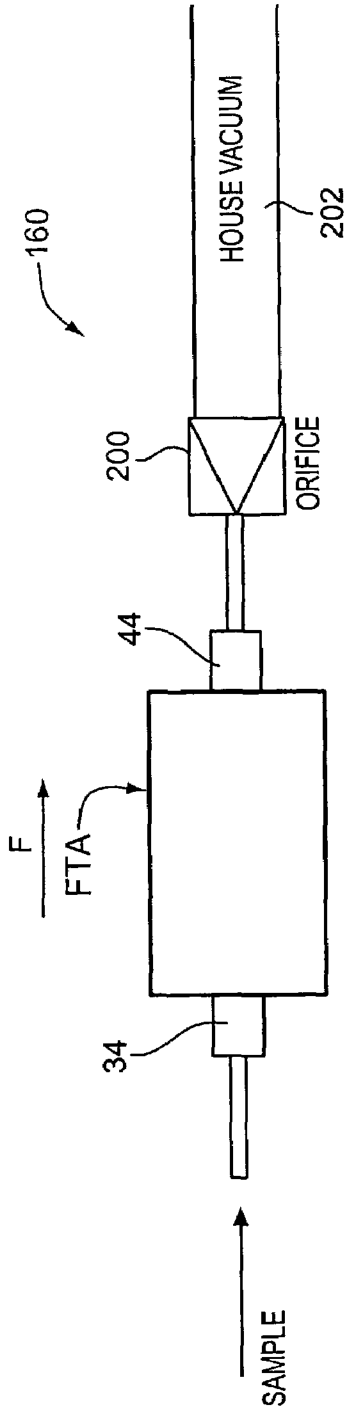
FIG. 10 depicts another aspect of the invention, having a vacuum connected downstream of any FTA according to the invention, for monitoring ambient air or other fluids.

The FTA of this invention has been described above in reference to a continuous fluid flow into influent tube 38 and out through effluent tube 46. A further aspect of this invention, though, measures MC within a non-pressurized or non-flowing ambient fluid, such as air. Referring to FIG. 10, an example structure for this aspect and its measuring of MC within a non-pressurized ambient air, or “AAMB” will be described.

The FIG. 10 example monitoring system 160 includes an FTA, which may be any of the above-described and depicted variations of the FTA of this invention, combined with an orifice/flow control unit 200 and a vacuum source 202. Orifice/flow control unit 200 may, for example, be a critical orifice, or may be a needle valve selected from among the plurality of commercially available units which are known in the relevant arts. The level of the vacuum provided by source 202 measured in, for example, Pascals, is selected based on the desired pressure and/or velocity of the flow of the MMB sample through the FTA.

The FTA is shown in FIG. 10 as being proximal to the ambient air AAMB. This depiction is only for purposes of description, and is not a limitation. In actuality, the location of the FTA relative to the sample position (not shown) from which the ambient air AAMB is drawn is dictated, in part, by the physical environment and, further, it may be a matter of design choice. Therefore, it is contemplated that an extension (not shown), either rigid or flexible, may be attached to FTA influent connection 34.

An example operation of the FIG. 10 aspect of this invention is as follows. First, any sampling extension (not shown) that is used is attached to influent connection 34, using any conventional attachment means. Next, vacuum source 202 is connected to orifice/flow control unit 200 which, in turn, is connected to FTA effluent connector 44. Orifice/flow control unit 200 is then switched open, by either manual or automatic means (not shown), and held open for a predetermined length of time and switched off.

Figure 11:
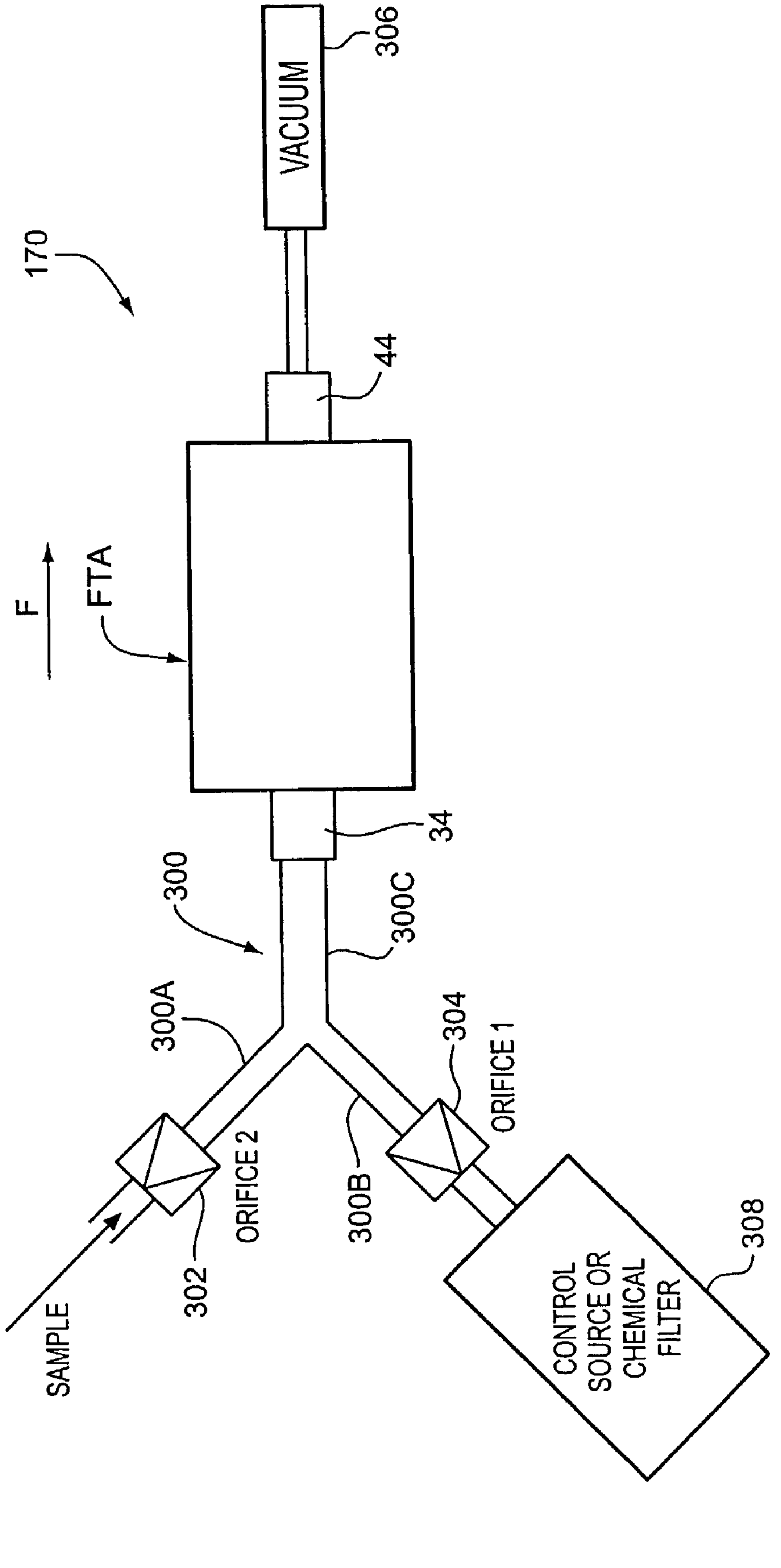
FIG. 11 depicts a further aspect of the invention, comprising an FTA according to the invention combined with a sample dilution apparatus.

FIG. 11 shows a further aspect of this invention, a molecular contaminant monitoring system 170 comprising any of the above-described and depicted variations of the inventive FTA , combined with a sample dilution feature. It is contemplated that, in some instances, the MC level of the SAMPLE fluid may be so high that it considerably shortens the life of the measurement SAW, or other piezoelectric crystal within the FTA. The FIG. 11 example solves the above-identified problem by diluting the SAMPLE fluid with diluting fluid substantially free of MC, and of particle contaminants, before entering the FTA. This sample dilution aspect would typically be used in conjunction with the above-described aspect for measuring contaminants within a non-pressurized SAMPLE fluid.

The example of this sample dilution aspect depicted by FIG. 11 includes an FTA and a flow-splitter 300, flow splitter 300 having a sample port 300A, a dilution source port 300B, and a mixture output port 300C. A sample fluid flow regulator comprising flow control orifice 302 is connected to sample (first) entry port 300A, and a dilution fluid flow regulator comprising flow control orifice 304 is connected to the distal end of dilution source (second) entry port 300B. Each of orifices 302, 304 is a controllable flow rate orifice, having either a manually actuated flow adjustment mechanism, or a servo-motor mechanism, each of these types being well known and available from a number of commercial vendors. The orifices may be electronically controlled to provide a precise ratio of the contaminant free gas and the SAMPLE gas.

As shown in FIG. 11, a vacuum source 306 is connected to the distal end of the effluent tube, for substantially the same purpose as vacuum source 202 described in reference to FIG. 10. Sample port 300A of flow-splitter 300 is connected to a non-pressurized sample of a subject fluid SAMPLE, in substantially the same manner as the SAMPLE is connected to influent tube 22 of the FIG. 11 example described above.

A control source 308 is connected to dilution flow control orifice 304. Control source 308 outputs a diluting fluid, which may or may not be chemically identical to the SAMPLE fluid, but which is preferably conditioned by a chemical filter (not shown), or other purifying means, to remove substantially all contaminants. Since the diluting fluid output from control source 308 is substantially free of MC, adjusting the proportional difference between the flow rate through sample flow control orifice 302 and the flow rate through dilution flow control orifice 304, lowers the MC levels of the fluid entering the FTA by the same proportional difference.

Referring to FIG. 11, it will be understood that the depicted Y-tube structure of flow splitter 300, and of the connection and arrangement of flow control orifices 302, 304, is only an example, which was selected for purposes of describing this feature. Other structures and methods for sample dilution are contemplated by this invention. For example, multi-passage valve body (not shown) with integrated flow metering devices (not shown) could be used instead of Y-tube 300 with attached flow control orifices 302, 304.

Figure 12:
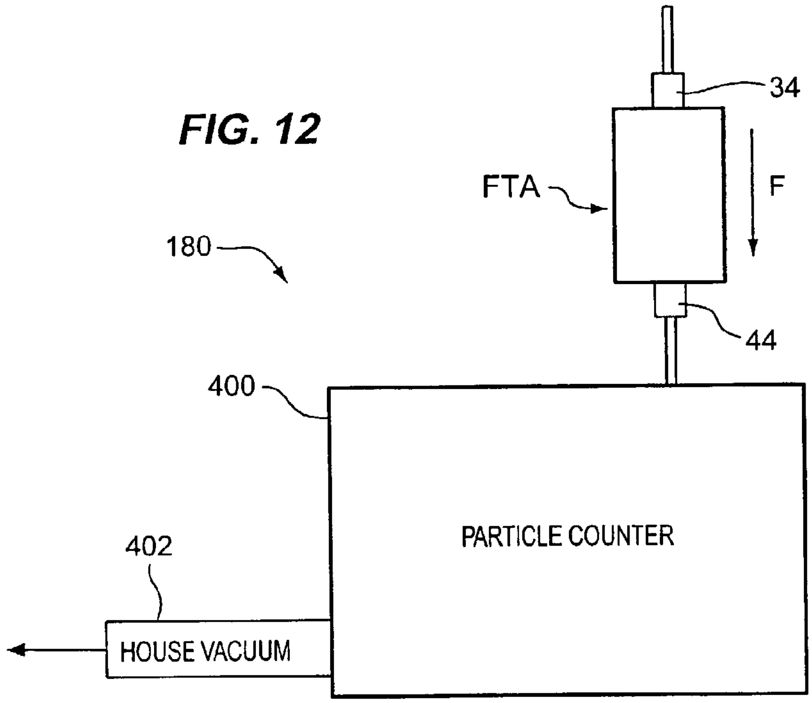
FIG. 12 depicts another aspect of the invention, comprising an FTA according to the invention and having a particulate contaminant counter connected downstream.

Many applications in which the present invention can be used require monitoring of particulate contamination, which has its own effects in product processing. Referring to FIG. 12, the monitoring of particulate contamination is easily accomplished with the present invention, simply by connecting a particle contaminant counter 400 downstream of the FTA to provide another exemplary monitoring system 180. The FTA, as identified above, is an FTA according to, and including, a combination of aspects and features described in reference to FIGS.2–7 and 9. An example of a commercially available particulate counter that may be used for item 400 is the AIRNET™ model available from Particle Measuring Systems, Inc., Boulder Colo. Alternatively, the particle counter may be made integral with the FTA.

Particle counter 400 as shown in FIG. 12 exploits the structure and operation of tapered nozzle 38A and tapered port 22A, described in reference to FIG. 3, as well as similar nozzle-port arrangements described in reference to FIG. 6, namely, guiding particulate contaminants through the FTA, while effecting diffusion of MC into diffusion chamber passage 19. As previously described, the form and structure of tapered nozzle 38A and tapered port 22A, and tapered nozzle 26A' and tapered port 22A", cause the particulate contamination to be substantially passed through and not monitored by the FTA. Therefore, by simply connecting a particulate contaminant counter 400 to the FTA, a combination monitoring system for both MC and particulate contamination is obtained. The particulate counter is preferably connected downstream of the FTA, as shown in FIG. 12, to avoid MC contamination of the sample fluid entering the FTA.

Figure 13:
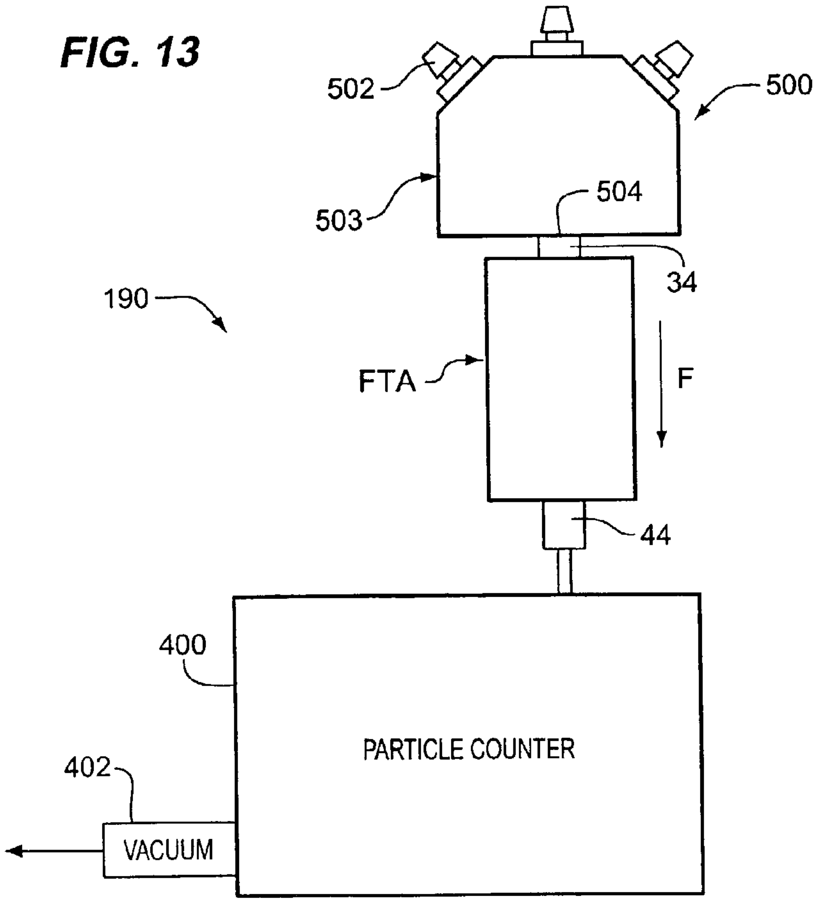
FIG. 13 depicts a further aspect of the invention, comprising the example apparatus of FIG. 12 combined with an ensemble manifold.

FIG. 13 depicts a further monitoring system 190 according to the invention, comprising the example monitoring system 180 of FIG. 12 combined with an ensemble manifold 500. The example of this aspect of the invention depicted in FIG. 13 includes a particulate contaminant counter 400, which was described previously. Counter 400, though, can be omitted. Preferably, ensemble manifold 500 is in accordance with co-pending U.S. application Ser. No. 09/638,366, filed Aug. 15, 2000, which is hereby incorporated by reference. Ensemble manifold 500, as it is described in co-pending U.S. application Ser. No. 09/638,366, differs from other multi-inlet manifolds by having a plurality of entry or inlet sample ports 502, a junction area 503 in which the sample fluids from all of the sample sources are combined, and an outlet or delivery port 504 through which the combined sample stream flows. In this description, delivery port 504 is connected to influent connection 34 of the FTA. As described in co-pending application Ser. No. 09/638,366, there are multiple benefits and advantages of ensemble manifold 500 over conventional multi-port collection systems, as the latter typically use a multiplexed stepper to sequentially select and sample the input ports, one at a time. The advantages include a continuous monitoring of the ensemble of sample streams entering sample ports 502, and a reduction in the amount of sample fluid which is drawn but, instead of being monitored, is simply routed to a waste exhaust.

Referring to FIG. 13, each of sample ports 502 typically receives sample fluids through, for example, a flexible plastic tube (not shown) connected to it and to a particular sample probe (not shown) at a sample point (not shown) within the monitored environment. To avoid effects of outgassing by the materials in the fluid conduction from sample ports 502 to the sample probes, the connection, such as the example plastic tubes, may be lined with a protective material.

Preferably, the drawing of fluid samples is conducted isokinetically. For this reason, the sampling probes preferably are isokinetic sampling probes.

Referring to FIG. 13, the FTA operates as previously described above in detecting MC within the combined fluid flow, reflecting the aggregation of the fluids received through each of input ports 502.

Figure 14:
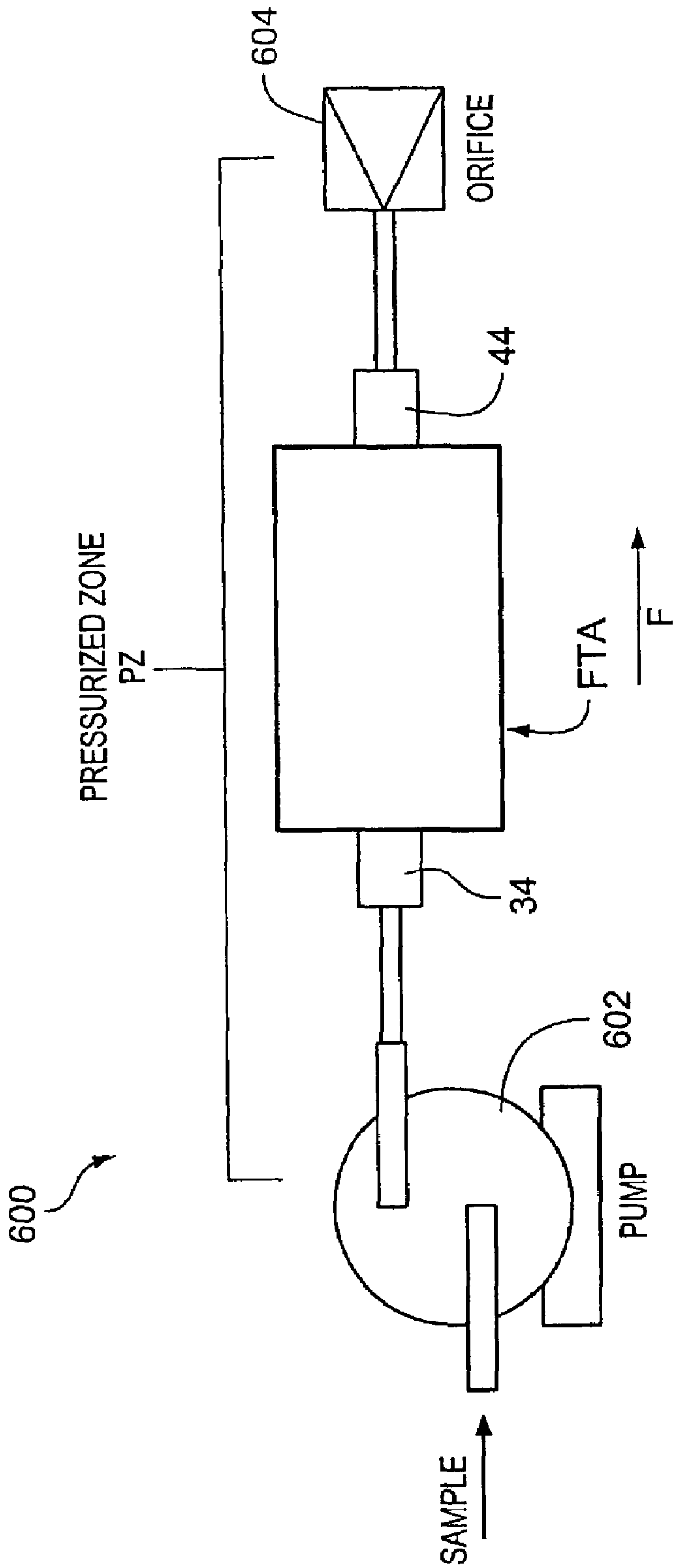
FIG. 14 depicts another aspect of the invention, comprising an FTA according to this invention combined with an air pump for pressurization of samples.

FIG. 14 depicts a further monitoring system 600 according to the invention, comprising an FTA combined with a pump 602 and a fluid flow regulator such as restrictive orifice 604 for pressurization of the sample fluid within the FTA. The pressurization zone, labeled PZ, results from the back pressure within the FTA due to restrictive orifice 604. The present inventors have identified that, at increased fluid pressures at the surface of SAW 56, the MC molecules are more tightly packed, resulting in an increased collision frequency between the molecules and the SAW 56 surface. This increases the rate at which the MC causes SMC accumulation on the SAW 56 surface. As a result, MC levels that, without pressurization may not have created enough SMC on the SAW 56 surface in a given sample period to be detectable, will effect a detectable change in the SAW 56 frequency. The system of FIG. 14 thus provides increased sensitivity over the system of FIG. 10 when measuring, for example, MC within an ambient fluid.

Figure 15:
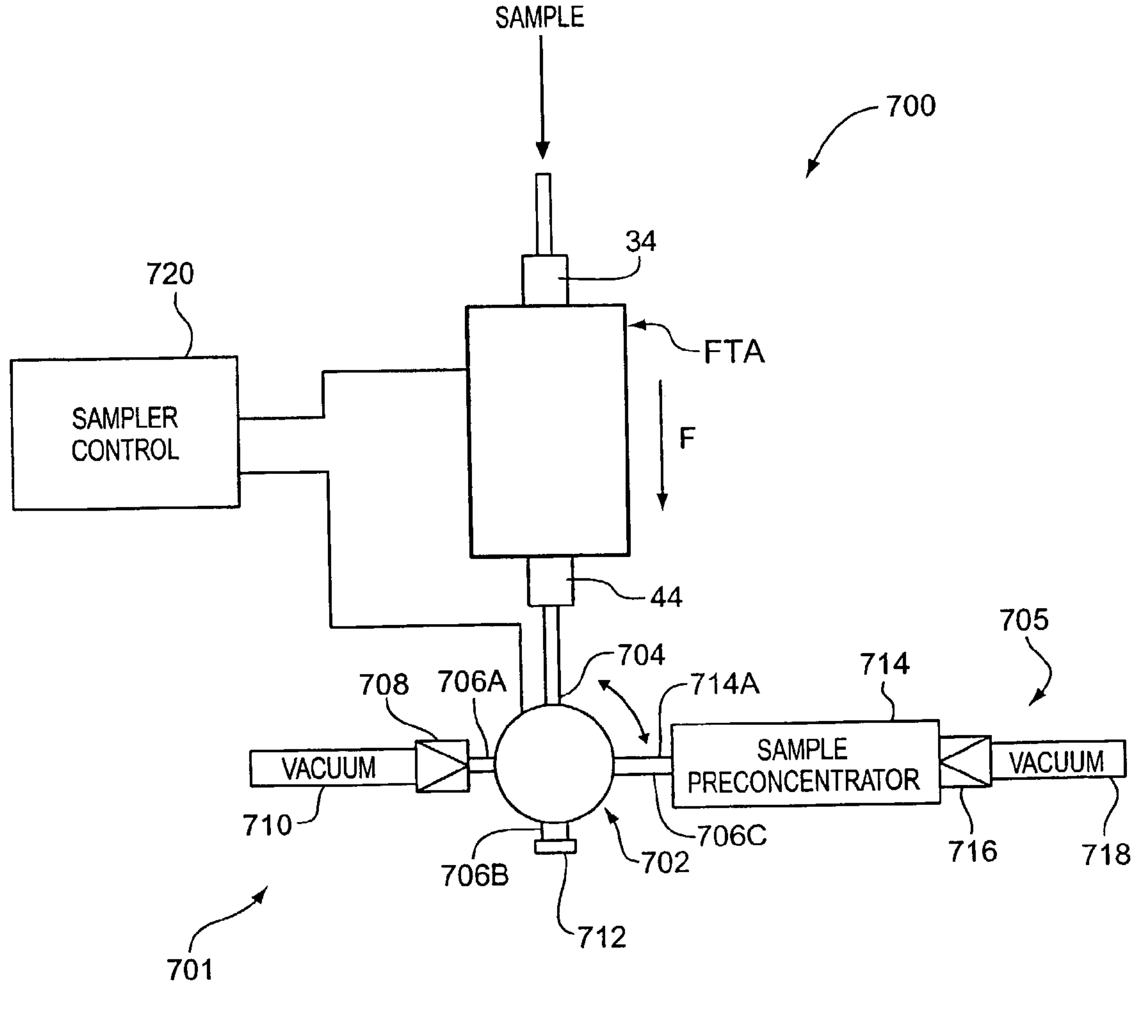
FIG. 15 depicts a further aspect of the invention, comprising an FTA according to this invention combined with a fluid sample preconcentrator unit triggered by the FTA.

FIG. 15 depicts a further monitoring system 700 according to the invention, comprising an FTA combined with a fluid sample preconcentrator which the FTA triggers to intake samples upon detection of MC levels over a threshold value or the rate of change of the sensor output signal SMC(t) exceeding a predetermined rate of change threshold.

The FIG. 15 example of this FTA-triggered sampling feature includes an FTA with its influent connector 34 connected to receive a SAMPLE fluid and a collection assembly 705. Collection assembly 705 includes a solenoid controlled port selection valve 702 connected downstream of the FTA, a sample collector 716, flow regulator 716, and a vacuum source 718. Solenoid controlled valve 702 has an input port 704 connected to the FTA effluent tube connector 44, a first output port 706A connected through a fluid flow regulator comprising first orifice 708 to a first vacuum source 710, a second output port 706B capped by a cap plug 712, and a third output port 706C which is connected to input 714A of a sample collector or preconcentrator 714. Sample preconcentrator 714 connects through a second fluid flow regulator comprising a second orifice 716 to a second vacuum source 718. The solenoid-controlled valve 702 of FIG. 15 has three states. The first state is a flow path from input port 704 to second output port 706B, which is capped. In this state, there is no flow through the FTA. The second state is a flow path from input port 704 to first output port 706A. In this state, the flow through the FTA is in accordance with the flow described in reference to FIG. 10. The third state is a flow path from input port 704 to third output port 706C. In this state, the sample is input to sample preconcentrator 714.

A trigger controller 720, which may be the computer 86 of FIG.3, receives the SMC(t) signal from the FTA and, using a standard triggering algorithm based on the magnitude and rate of change of the identified signals, generates a valve control signal 720. In the FIG. 15 example, valve control signal 720 switches the solenoid-controlled valve 702 between the three above-described states.

A typical operation of the FIG. 15 example system begins by generating valve control signal 720 to switch solenoid-controlled valve 702 to the second state, causing the sample fluid to flow through the FTA, first orifice 708, and into first vacuum 710. MC within the sample flow passing through the FTA causes changes in the SMC(t) signals, as described above. If SMC(t), or its rate of change, is above a predetermined threshold, trigger controller 720 generates a valve control signal 720 that switches valve 702 to the third state, causing the sample to flow into sample preconcentrator 714. After a predetermined number of repetitions of the sample flow, triggered by the FTA, into sample preconcentrator 714, its contents are analyzed using conventional analytical techniques.

An alternative to the structure 701 depicted in FIG. 15 is a commercially available, off-the-shelf, self-contained air sampler connected downstream of the FTA. The only required modification would be an interface between the SMC(t) signals output from the FTA and the control inputs (not shown) of such an air sampler. The sample collector/preconcentrator 714 may comprise other commercially available, off-the-shelf samplers such as a pump, a sorbent tube, an impinger, various plumbing arrangements, etc.

The FTA-triggered air sampling described above exploits the sensitivity of the FTA for a directed collection of fluid samples for subsequent identification of MC chemical species. It is further contemplated that chemically selective membrane 122 described above can be used for additional selectivity in sample collection and preconcentration.

Figure 16:
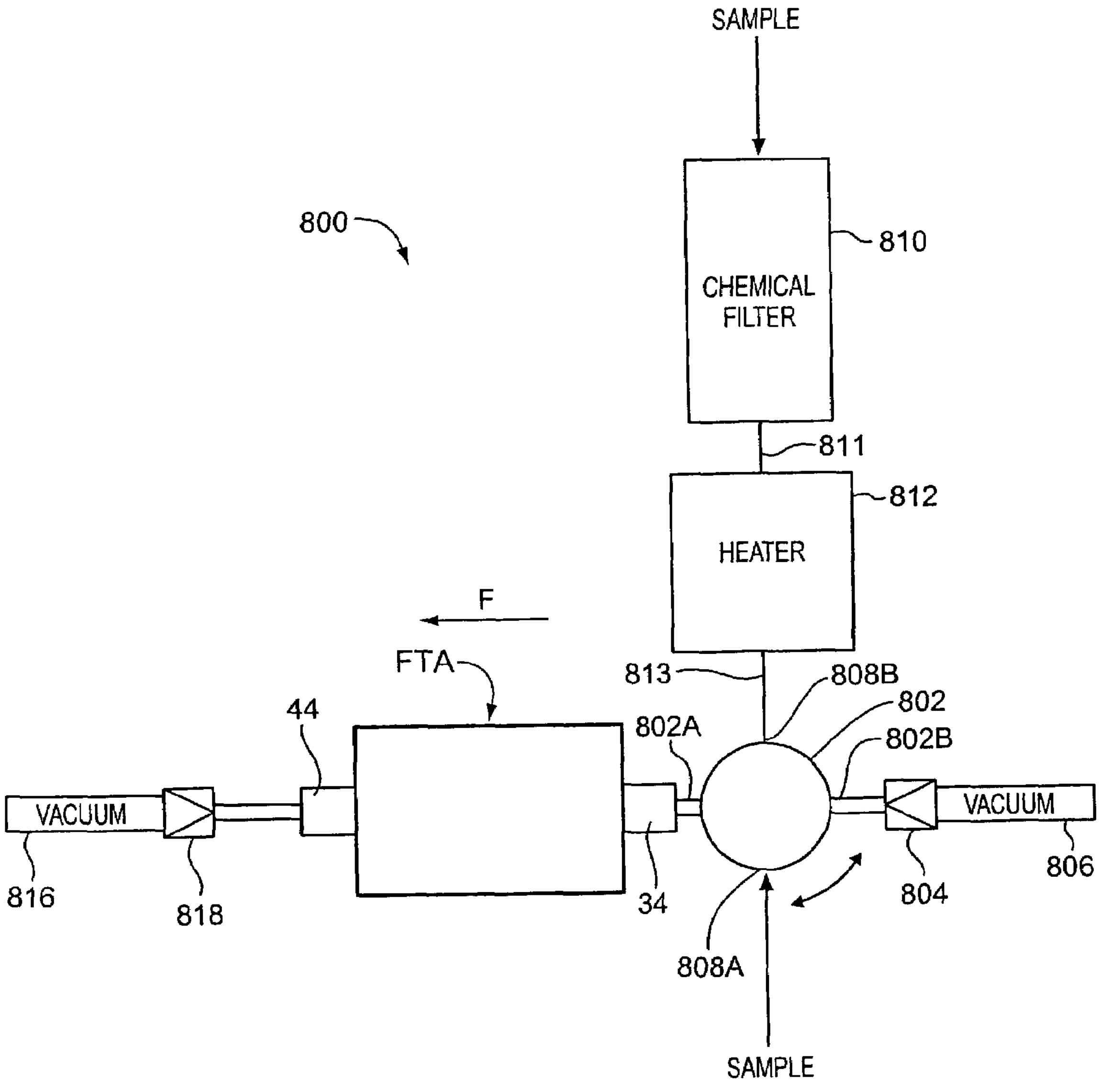
FIG. 16 depicts another aspect of the invention, comprising an FTA according to this invention combined with a selectively controlled sample pre-heater.

FIG. 16 shows an example of a monitoring system 800 according to the invention, which combines the described FTA with a controlled sample pre-heating feature. This feature provides for alternating the sample source between a preheated source and an unheated source. By alternating the sources, the temperature of the sample flow through the FTA varies, which allows for the thermal desorption of certain MC chemical compounds. This, in turn, permits detection of certain MCs that cause irreversible, or pseudo-irreversible SMC on the surface of measurement SAW 56. Pseudo-reversible SMC is contamination that evaporates from the surface, but slowly; for example if the contaminant source is removed, over a period of days or weeks pseudo-reversible contamination will remove itself from the surface at room temperature.

The example structure depicted by FIG. 16 comprises an FTA according to and having the embodiments, aspects and features described above, with its influent connector 34 connected to a first output port 802A of a solenoid-controlled valve 802. A second output port 802B of solenoid-controlled apportionment valve 802 connects through a first orifice 804 to a first vacuum source 806. Solenoid-controlled apportionment valve 802 has a first and a second receiving or entry port, labeled 808A and 808B, respectively. First input port 808A receives unheated and, in this example, unfiltered SAMPLE fluid. Second input port 808B receives SAMPLE fluid that has been conditioned by a chemical filter 810 and a heater 812. Chemical filter 810 preferably removes substantially all of the contaminants from the sample gas and directs it to the receiving port 811 of heating chamber 812. The heating chamber exit port 813 is connected to the FTA entry passage via valve 802. A second vacuum source 816 connects to effluent connector 44 of the FTA.

Valve 802 is designed so that when vacuum source 806 is connected to one of ports 808A or 808B, vacuum source 816 is connected to the other one of ports 808A and 808B. This promotes stability in the measurements, prevents stagnation of fluid in the heater 812, filter 810, tubing, ports or other part of the system, which could cause a spike of contamination harmful to the detecting surfaces when the position of the valve is changed.

By controlling solenoid-controlled valve 802, the SAMPLE flow through the FTA can be alternated between heated and/or chemically filtered SAMPLE and unheated SAMPLE. Varying the temperature would, in certain instances, create a reversible contaminant/surface interaction at the surface of SAW 56, or at the surface of another piezoelectric crystal substituted for the SAW, from a pseudo-irreversible surface interaction. It is contemplated that this feature would likely be useful for charge-transfer sensor coatings targeting MC of the ammonia/amines kind. Heater 812 is optional in one embodiment, and chemical filter 810 is optional in another embodiment.

A valve, such as 802, may also be used to dilute the SAMPLE entering at entry port 808A with gas substantially free of contaminants. As discussed above, dilution of the contaminants in the gas flowing into FTA reduces the sensitivity of the sensor, and at the same time increases the life of the SAW surface 61. This feature is particularly useful for measurements in highly contaminated areas.

Used without the heater 812, the system 800 is also useful to improve sensitivity to highly volatile compounds, such as ammonia. The system 800 can alternately sample contaminant-free air or a controlled, known, clean gas source and unaltered ambient air. This approach allows the FTA to determine a background or "zero" level that can be compared to the signal generated from exposure to the ambient air over relatively short time frames. By keeping the cycling frequency sufficiently large, highly volatile compounds, including ammonia, may be distinguished from the lower frequency fluctuations of low volatility contaminants. This can also allow one FTA unit to simultaneously monitor organic condensables and ammonia. Preferably the cycling period is less than a day, and preferably ranges from ranges from about a second to several hours. Most preferably, it is less than an hour.

It should be understood that the particular embodiments shown in the drawings and described within this specification are for purposes of example and should not be construed to limit the invention which will be described in the claims below.

We claim:

1. A molecular contaminant monitoring system comprising:

a housing forming a diffusion chamber;

a diffusion chamber entry passage extending through said housing;

a diffusion chamber exit passage extending through said housing;

a detection surface exposed to the interior of said diffusion chamber; and a sensor physically or electrically connected to said detection surface and providing a sensor output signal characteristic of molecular contaminants on said detection surface;

said diffusion chamber entry passage and said diffusion chamber exit passage adapted and located such that when a fluid containing molecular contaminants and particles is flowed through said entry passage above a predetermined flow rate, the majority of said particles passing through said entry passage are channeled into said exit passage whiles portion of said molecular contaminant passing through said entry passage moves into said diffusion chamber essentially solely by the process of molecular diffusion, said portion of said molecular contaminant being large enough to be sensed by said sensor; and wherein said diffusion chamber entry passage includes a diffusion chamber inlet port and a nozzle surrounding said chamber inlet port, and said diffusion chamber exit passage includes a diffusion chamber outlet port and a funnel surrounding said chamber outlet port.

2. A molecular contaminant monitoring system as in claim 1, wherein said sensor comprises a piezoelectric device.

3. A molecular contaminant monitoring system as in claim 1, further comprising:

a hermetically sealed reference chamber;

a reference surface substantially identical to said detection surface, exposed to the interior of said hermetically sealed reference chamber; and wherein said detector circuit includes:

a detector circuit associated with said detection surface and generating a detection signal reflecting a condition of said detection surface;

a reference circuit associated with said reference surface and generating a reference signal reflecting a condition of the reference surface; and a comparison circuit receiving said detection signal and said reference signal and generating said sensor output signal reflecting a difference between said detection signal and said reference signal.

4. A molecular contaminant monitoring system as in claim 3 wherein said detector circuit further includes an oscillator circuit connected to said detection surface such that its oscillaring signal frequency varies in accordance with molecular contaminants on said detection surface, and said reference circuit comprises a reference oscillator circuit generating a reference signal having an oscillating frequency reflecting a condition of said reference surface.

5. A molecular contaminant monitoring system as in claim 1, further comprising:

an environment sensor for detecting at least one of a temperature and a humidity of an externally generated fluid flowing into diffusion chamber and for generating an environment signal in response; and a compensator processor receiving said environment signal and said sensor output signal, and generating a corrected sensor output signal.

6. A molecular contaminant monitoring system as in claim 1, wherein said nozzle has a taper T, and wherein said funnel also has the same taper T, wherein said nozzle and funnel are substantially aligned on a common axis.

7. A molecular contaminant monitoring system as in claim 6 wherein said nozzle and said funnel and have a spacing from one another, and wherein said taper T and said spacing are such that, within a predetermined range of flow rates of said fluid, substantially all of said particles passing through said entry passage are channeled into said exit passage.

8. A molecular contaminant monitoring system as in claim 1 and further including a vacuum source connected to said diffusion chamber exit passage.

9. A molecular contaminant monitoring system as in claim 1 and further comprising a heater for heating said fluid.

10. A molecular contaminant monitoring system as in claim 9 wherein said heater includes a heating chamber, a heating chamber receiving port, and a heating chamber exit port, said heating chamber exit port connected to said diffusion chamber entry passage.

11. A molecular contaminant monitoring system as in claim 1 and further comprising a plurality of fluid entry ports connected to said diffusion chamber entry passage.

12. A molecular contaminant monitoring system as in claim 1 wherein said test surface and said detection surface comprise different surface materials.

13. A molecular contaminant monitoring system comprising:

a housing forming a diffusion chamber;

a diffusion chamber entry passage extending through said housing;

a diffusion chamber exit passage extending through said housing;

a detection surface exposed to the interior of said diffusion chamber; and a sensor physically or electrically connected to said detection surface and providing a sensor output signal characteristic of molecular contaminants on said detection surface;

said diffusion chamber entry passage and said diffusion chamber exit passage adapted and located such that when a fluid containing molecular contaminants and particles is flowed through said entry passage above a predetermined flow rate, the majority of said particles passing through said entry passage are channeled into said exit passage while a portion of said molecular contaminant passing through said entry passage moves into said diffusion chamber essentially solely by the process of molecular diffusion, said portion of said molecular contaminant being large enough to be sensed by said sensor;

and further comprising a particle counter connected to said exit port.

14. A molecular contaminant monitoring system comprising:

a housing forming a diffusion chamber;

a diffusion chamber entry passage extending through said housing;

a diffusion chamber exit passage extending through said housing;

a detection surface exposed to the interior of said diffusion chamber; and a sensor physically or electrically connected to said detection surface and providing a sensor output signal characteristic of molecular contaminants on said detection surface;

said diffusion chamber entry passage and said diffusion chamber exit passage adapted and located such that when a fluid containing molecular contaminants and particles is flowed through said entry passage above a predetermined flow rate, the majority of said particles passing through said entry passage are channeled into said exit passage while a portion of said molecular contaminant passing through said entry passage moves into said diffusion chamber essentially solely by the process of molecular diffusion, said portion of said molecular contaminant being large enough to be sensed by said sensor;

and further comprising: a heating chamber, a heater for heating a fluid in said chamber, a heated fluid exit port, a valve having a first receiving port connected to said heated fluid exit port, a second receiving port connected to an external sample fluid source, and a valve output port;

and said valve is adapted for connecting a selected one from said first receiving port and said second receiving port to said valve output port in response to an externally generated valve control signal.

15. A molecular contaminant monitoring system comprising:

a housing forming a diffusion chamber;

a diffusion chamber entry passage extending through said housing;

a diffusion chamber exit passage extending through said housing;

a detection surface exposed to the interior of said diffusion chamber; and a sensor physically or electrically connected to said detection surface and providing a sensor output signal characteristic of molecular contaminants on said detection surface;

said diffusion chamber entry passage and said diffusion chamber exit passage adapted and located such that when a fluid containing molecular contaminants and particles is flowed through said entry passage above a predetermined flow rate, the majority of said particles passing through said entry passage are channeled into said exit passage while a portion of said molecular contaminant passing through said entry passage moves into said diffusion chamber essentially solely by the process of molecular diffusion, said portion of said molecular contaminant being large enough to be sensed by said sensor;

and further including; a plurality of fluid entry ports connected to said diffusion chamber entry passage and an ensemble manifold, said ensemble manifold connected between said plurality of entry ports and said diffusion chamber entry passage.

16. A molecular contaminant monitoring system as in claim 15 and further comprising a particle counter connected to said exit port.

17. A molecular contaminant monitoring system as in claim 15 wherein said plurality of fluid entry ports include a first entry port and a second entry port, and said system further includes a first fluid flow regulator connected to said first entry port and a second fluid flow regulator connected to said second entry port.

18. A molecular contaminant monitoring system as in claim 17 wherein said first and second fluid flow regulators comprise an adjustable metering device.

19. A molecular contaminant monitoring system as in claim 18 wherein said adjustable metering devise comprises an adjustable orifice.

20. A molecular contaminant monitoring system as in claim 17 and further including a source of fluid substantially free of said contaminant, said source connected to said first entry port.

21. A molecular contaminant monitoring system as in claim 20 wherein said source of fluid substantially free of said contaminant comprises a chemical filter.

22. A molecular contaminant monitoring system as in claim 21 and further including a vacuum source connected to said diffusion chamber exit passage.

23. A molecular contaminant monitoring system as in claim 15 wherein said plurality of fluid entry ports include a first entry port and a second entry port, said system further including a port selection valve connected between said first and second entry ports and said diffusion chamber entry passage.

24. A molecular contaminant monitoring system as in claim 23 and further including a source of fluid substantially free of said contaminant, said source connected to said first entry port, whereby, by manipulating said port selection valve a user can alternatively select ambient fluid and contaminant free fluid for passage to entry passage.

25. A molecular contaminant monitoring system as in claim 24 and further including a fluid heater connected between said source of fluid substantially free of said contaminant and said port selection valve.

26. A molecular contaminant monitoring system as in claim 24 and further including a first vacuum source connected to said diffusion chamber exit passage.

27. A molecular contaminant monitoring system as in claim 26 and further including a fluid flow regulator connected between said vacuum source and said diffusion chamber exit passage.

28. A molecular contaminant monitoring system as in claim 26 and further including a second vacuum source connected to said port selection valve, said port selection valve arranged so that when said first vacuum source is connected to one of said first and second entry ports said second vacuum source is connected to the other of said first and second entry ports.

29. A molecular contaminant monitoring system as in claim 28 and further including a first fluid flow regulator connected between said first vacuum source and said diffusion chamber exit passage and a second fluid flow regulator connected between said second vacuum source and said port selection valve.

30. A molecular contaminant monitoring system as in claim 29 and further including a fluid hearer connected between said source of fluid substantially free of said contaminant and said port selection valve.

31. A molecular contaminant monitoring system comprising:

a housing forming a diffusion chamber;

a diffusion chamber entry passage extending through said housing;

a diffusion chamber exit passage extending through said housing;

a detection surface exposed to the interior of said diffusion chamber; and a sensor physically or electrically connected to said detection surface and providing a sensor output signal characteristic of molecular contaminants on said detection surface;

said diffusion chamber entry passage and said diffusion chamber exit passage adapted and located such that when a fluid containing molecular contaminants and particles is flowed through said entry passage above a predetermined flow rate, the majority of said particles passing through said entry passage are channeled into said exit passage while a portion of said molecular contaminant passing through said entry passage moves into said diffusion chamber essentially solely by die process of molecular diffusion, said portion of said molecular contaminant being large enough to be sensed by said sensor;

and further comprising: an apportioning valve having a first receiving port, a second receiving port, a mixed fluid output port, and said apportionment valve connected to an externally generated apportionment signal and establishing a flow path between said first receiving port, said second receiving port, and said mixed fluid output port such that a fluid exiting from said mixed fluid output port comprises a ratio, determined by said apportionment signal, of a fluid entering said first receiving port and a fluid entering said second receiving port.

32. A molecular contaminant monitoring system comprising:

a housing forming a diffusion chamber;

a diffusion chamber entry passage extending through said housing;

a diffusion chamber exit passage extending through said housing;

a detection surface exposed to the interior of said diffusion chamber; and a sensor physically or electrically connected to said detection surface and providing a sensor output signal characteristic of molecular contaminants on said detection surface;

said diffusion chamber entry passage and said diffusion chamber exit passage adapted and located such that when a fluid containing molecular contaminants and particles is flowed through said entry passage above a predetermined flow rate, the majority of said particles passing through said entry passage are channeled into said exit passage while a position of said molecular contaminant passing through said entry passage moves into said diffusion chamber essentially solely by the process of molecular diffusion, said portion of said molecular contaminant being large enough to be sensed by said sensor;

and further comprising a collection assembly connected to said diffusion chamber exit passage.

33. A molecular contaminant monitoring system as in claim 32 wherein said collection assembly comprises one or more of the following; a sorbent material, an impinger, and a by-passable pumping route.

34. A molecular contaminant monitoring system as in claim 33 and further including a first exit port and a second exit port, and said collection assembly includes an exit port selection valve located between said diffusion chamber exit passage and said exit ports, and a collector connected to said second exit port.

35. A molecular contaminant monitoring system as in claim 34 and further comprising a sampler controller for producing a selection valve control signal responsive to said sensor output signal.

36. A molecular contaminant monitoring system as in claim 35 wherein said sampler controller controls said selection valve to direct fluid to said collector in response to said sensor output signal either exceeding a predetermined output signal threshold or the rate of change of said sensor output signal exceeding a predetermined rate of change threshold.

37. A molecular contaminant monitoring system comprising:

a housing forming a diffusion chamber;

a diffusion chamber entry passage extending through said housing;

a diffusion chamber exit passage extending through said housing;

a detection surface exposed to the interior of said diffusion chamber; and a sensor physically or electrically connected to said detection surface and providing a sensor output signal characteristic of molecular contaminants on said detection surface;

said diffusion chamber entry passage and said diffusion chamber exit passage adapted and located such that when a fluid containing molecular contaminants and particles is flowed through said entry passage above a predetermined flow rate, the majority of said particles passing through said entry passage are channeled into said exit passage while a portion of said molecular contaminant passing through said entry passage moves into said diffusion chamber essentially solely by the process of molecular diffusion, said portion of said molecular contaminant being large enough to be sensed by said sensor;

and further comprising a gas pressurizer connected to said diffusion chamber entry passage.

38. A molecular contaminant monitoring system as in claim 37 and further comprising a fluid flow regulator connected to said diffusion chamber exit passage.

39. A molecular contaminant monitoring system comprising;

a housing forming a diffusion chamber;

a diffusion chamber entry passage extending through said housing;

a diffusion chamber exit passage extending through said housing;

a detection surface exposed to the interior of said diffusion chamber; and a sensor physically or electrically connected to sail detection surface and providing a sensor output signal characteristic of molecular contaminants on said detection surface;

said diffusion chamber entry passage and said diffusion chamber exit passage adapted and located such that when a fluid containing molecular contaminants and particles is flowed through said entry passage above a predetermined flow rate, the majority of said particles passing through said entry passage are channeled into said exit passage while a portion of said molecular contaminant passing through said entry passage moves into said diffusion chamber essentially solely by the process of molecular diffusion, said portion of said molecular contaminant being large enough to be sensed by said sensor;

and further comprising a test surface adapted to collect said molecular contamination and located to sample the same fluid as said detection surface.

40. A molecular contaminant monitoring system as in claim 39, and further comprising:

a portal through said housing for passing said test surface; and a removable cover on said portal for enclosing said test surface.

41. A molecular contaminant monitoring system as in claim 39 wherein said test surface and said detection surface comprise the same surface material.

42. A molecular contaminant monitoring system as in claim 39 wherein said test surface and said detection surface comprise different surface materials.

43. A molecular contaminant monitoring system comprising;

a housing forming a diffusion chamber;

a diffusion chamber entry passage extending through said housing;

a diffusion chamber exit passage extending through said housing;

a detection surface exposed to the interior of said diffusion chamber; and a sensor physically or electrically connected to said detection surface and providing a sensor output signal characteristic of molecular contaminants on said detection surface;

said diffusion chamber entry passage and said diffusion chamber exit passage adapted and located such that when a fluid containing molecular contaminants and particles is flowed through said entry passage above a predetermined flow rate, the majority of said particles passing through said entry passage are channeled into said exit passage while a portion of said molecular contaminant passing through said entry passage moves into said diffusion chamber essentially solely by the process of molecular diffusion, said portion of said molecular contaminant being large enough to be sensed by said sensor;

and further comprising a chemically selective membrane located between said detection chamber entry passage and said detection surface.

44. A molecular contaminant monitoring system comprising:

a fluid flow passage;

a detection surface;

a diffusion structure permitting a molecular contaminant from said fluid in said flow passage to diffuse to said detection surface while preventing particulates of the size of ten nanometers or greater in said fluid in said flow passage from reaching said detection surface with a statistical probability of greater than 99.9 percent; and a sensor physically or electrically connected to said detection surface and providing a sensor output signal characteristic of molecular contaminants on said detection surface;

wherein said diffusion structure comprises a chemically selective membrane located between said fluid flow passage and said detection surface.

45. A molecular contaminant monitoring system as in claim 44, wherein said fluid comprises a gas.

46. A molecular contaminant monitoring system as in claim 45 wherein said diffusion structure comprises: a diffusion chamber containing said detection surface; and an opening in said fluid flow passage communicating with said diffusion chamber.

47. A molecular contaminant monitoring system comprising:

a housing forming a diffusion chamber;

a diffusion chamber entry passage extending through said housing, having a receiving port external to said diffusion chamber, and a chamber inlet port internal to said diffusion chamber;

a diffusion chamber exit passage extending through said housing, having a chamber outlet port internal to said diffusion chamber and an exit port external to said diffusion chamber;

a detection surface exposed to the interior of said diffusion chamber, said chamber inlet port and said detection surface located so that a particle passing through said inlet port must make a turn of greater than sixty degrees to reach said detection surface; and a sensor physically or electrically connected to said detection surface and providing a sensor output signal characteristic of a molecular contaminant on said detection surface; and further comprising a particle detector connected to said exit port.

48. A molecular contaminant monitoring system comprising:

a housing forming a diffusion chamber;

a diffusion chamber entry passage extending through said housing;

a diffusion chamber exit passage extending through said housing;

a detection surface exposed to the interior of said diffusion chamber; and a sensor physically or electrically connected to said detection surface and providing a sensor output signal characteristic of molecular contaminants on said detection surface;

said diffusion chamber entry passage including a diffusion chamber inlet port and a nozzle surrounding said chamber inlet port, and said diffusion chamber exit passage including a diffusion chamber outlet port and a funnel surrounding said chamber outlet port.

49. A molecular contaminant monitoring system as in claim 48 wherein said nozzle has a taper T, and wherein said funnel also has the same taper T, and wherein said nozzle and funnel are substantially aligned on a common axis.

50. A method of real-time monitoring of a molecular contaminant in a first fluid, said method comprising:

flowing said fluid through a fluid passage;

while said fluid is flowing through said passage, diffusing a said molecular contaminant within said fluid in said fluid passage into a diffusion chamber at a diffusion rate such that, within a predetermined range of flow rates of said flowing fluid, a level of said molecular contaminant within said diffusion chamber tracks in a known relation with a level of said molecular contaminant within said fluid, and wherein the movement of said molecular contaminant into said diffusion chamber is essentially independent of said fluid flow;

detecting said molecular contaminant diffused into said diffusion chamber; and generating a sensor signal characteristic of said level of said molecular contaminant in said fluid.

51. A method as in claim 50 wherein said act of detecting comprises:

generating a detector acoustic wave on the surface of a detector piezoelectric crystal exposed to said contaminant; and determining a change in said detector acoustic wave due to said contaminant on said surface.

52. A method as in claim 51 wherein said act of determining comprises:

generating a reference acoustic wave on the surface of a reference piezoelectric crystal substantially identical to said detector piezoelectric crystal and having a surface exposed to a reference fluid, and comparing a parameter of said reference acoustic wave and said detector acoustic wave to provide said sensor signal.

53. A method as in claim 50 wherein said act of generating comprises:

detecting at least one of a temperature and a humidity of said fluid and providing a condition signal characteristic of at least one of said temperature and humidity; and adjusting said sensor signal based on said condition signal.

54. A method as in claim 50 and further including:

detecting particles in said fluid; and generating a particulate signal characteristic of said particles.

55. A method as in claim 50 wherein said fluid is a gas.

56. A method as in claim 55 wherein said act of detecting comprises detecting said contaminant on a surface within said diffusion chamber, and said method further comprises reversing a contaminant condition on said surface.

57. A method as in claim 56 wherein said act of reversing comprises heating at least a portion of said fluid.

58. A method as in claim 57 wherein said act of reversing comprises alternately directing said heated portion of said fluid and an unheated portion of said fluid into said fluid passage.

59. A method as in claim 55 and further including providing a second fluid substantially free of said molecular contaminant and alternately flowing said first fluid and said second fluid through said fluid passage.

60. A method as in claim 55 and further including the act of diluting said first fluid with a second fluid substantially free of said contaminant.

61. A method as in claim 60 wherein said act of diluting comprises:

providing a dilution signal indicative of a predetermined ratio of said first fluid and said second fluid; and combining said first fluid and said second fluid in accordance with said dilution signal.

62. A method as in claim 55 and further including collecting said contaminant in a removable collector.

63. A method as in claim 62 wherein said act of collecting includes preconcentrating said contaminant.

64. A method as in claim 55 and further comprising:

providing a plurality of sample ports each receiving a different fluid; and combining said fluids received through said sample ports and outputting the combined resultant fluid to said fluid passage.

65. A method as in claim 55 and further comprising:

pressurizing said fluid prior to flowing it through said fluid passage; and restricting the flow of said pressurized fluid exiting said fluid passage to provide a predetermined pressure level in said fluid passage.

66. A method as in claim 55 and further comprising removably securing a test surface in fluid communication with said diffusion chamber.

67. A method as in claim 55 and further including:

detecting particles n said fluid; and generating a particulate signal characteristic of said particles.

68. A method as in claim 55 wherein said step of diffusing comprises selectively passing said molecular contaminant through a chemically selective membrane.

69. A method as in claim 50 wherein said detecting comprises:

generating a detection signal reflecting a condition of a reference surface exposed to said diffusion;

generating a reference signal reflecting a condition of a reference surface located in a hermetically sealed reference chamber; and comparing said detection signal and said reference signal to generate said sensor signal.

70. A method as in claim 50 wherein said detecting comprises:

sensing at least one of a temperature and a humidity of said fluid and generating an environmental signal; and correcting said sensor output signal based on said environmental signal.

71. A method as in claim 50 wherein said flowing comprises alternately flowing said first fluid and a second fluid through said fluid passage, wherein said second fluid comprises a reference fluid substantially free of said contaminant.

72. A method of monitoring a molecular contaminant within a flowing fluid, comprising steps of:

transferring said flowing fluid through a fluid passage, with a diffusion path for said molecular contaminant within said fluid to diffuse from said fluid passage to a diffusion chamber, said diffusion path requiring a turn of sixty degrees or greater;

exposing a surface of a contaminant sensor to the interior of said diffusion chamber; and monitoring molecular contaminants on said surface.

73. A method as in claim 72 wherein said diffusion path is provided such that a particulate contaminant within said fluid does not, with any substantial statistical probability, enter said diffusion chamber.

* * * * *